United States Patent [19]

Karino et al.

[11] Patent Number: 5,188,928
[45] Date of Patent: Feb. 23, 1993

[54] SILVER HALIDE PHOTOGRAPHIC MATERIAL CONTAINING LIGHT ABSORBING COMPOUND

[75] Inventors: Yukio Karino; Tetunori Matushita, both of Kanagawa, Japan

[73] Assignee: Fuji Photo Film Co., Ltd., Kanagawa, Japan

[21] Appl. No.: 785,071

[22] Filed: Oct. 30, 1991

[30] Foreign Application Priority Data

Oct. 31, 1990 [JP] Japan .................. 2-295047

[51] Int. Cl.$^5$ ............................ G03C 1/492
[52] U.S. Cl. ..................... 430/513; 430/510; 430/517
[58] Field of Search .............. 430/513, 510, 517

[56] References Cited
U.S. PATENT DOCUMENTS 4,923,789  5/1990  Yagihara et al. .

Primary Examiner—Jack P. Brammer
Attorney, Agent, or Firm—Sughrue, Mion, Zinn, Macpeak & Seas

[57] ABSTRACT

A novel silver halide photographic material is provided comprising at least one silver halide emulsion layer on a support, wherein the emulsion layer or other hydrophilic colloidal layers comprise at least one compound represented by formula (I):

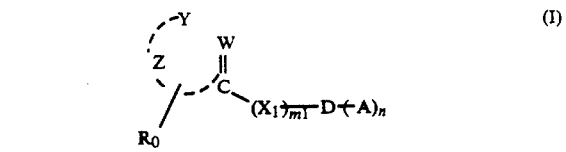

wherein W represents =N— or

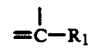

in which $R_1$ represents a hydrogen atom or a substituent; $R_0$ represents an alkyl group containing 10 or more carbon atoms or an aromatic group containing 12 or more carbon atoms; Z represents an atomic group which can form a heterocyclic group or a carbon ring; Y represents

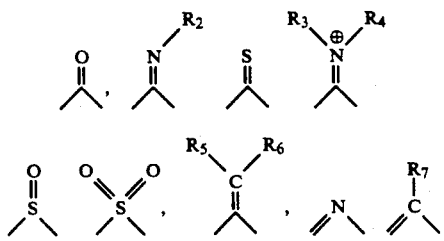

wherein $R_2$, $R_3$, $R_4$, $R_5$, $R_6$, and $R_7$ each represents a hydrogen atom or a substituent; $X_1$ represents a divalent group connected to carbon atom via a hetero atom contained therein; D represents a photogragraphic dye portion connected to $X_1$ via a hetero atom contained therein; A represents a water-solubilizing group; $m_1$ represents an integer 0 or 1; and n represents an integer 2 or more.

5 Claims, No Drawings

SILVER HALIDE PHOTOGRAPHIC MATERIAL CONTAINING LIGHT ABSORBING COMPOUND

FIELD OF THE INVENTION

The present invention relates to a silver halide photographic material. More particularly, the present invention relates to a silver halide photographic material comprising at least one layer containing a novel light absorbing compound which can be well incorporated in layers constituting the silver halide photographic material and can be decolored without leaving any color stain upon development.

BACKGROUND OF THE INVENTION

In general, a silver halide photographic material has heretofore comprised a light absorbing compound in a silver halide emulsion layer or other hydrophilic colloidal layers to absorb light of a specific wavelength for the purpose of adjusting sensitivity, color temperature of light and sensitivity balance in a multilayer color light-sensitive material, improving safety to safelight or inhibiting halation.

For example, in a silver halide photographic material comprising, on a support, hydrophilic colloidal layers such as a light-sensitive silver halide emulsion layer, it is necessary to control the spectral composition of light incident upon the silver halide emulsion layer to improve the photographic sensitivity during imagewise exposure to record images on the silver halide emulsion layer. In this case, the approach normally employed comprises incorporating a dye which absorbs light of a wavelength undesired by the light-sensitive silver halide emulsion layer in a hydrophilic colloidal layer present farther from the support than the light-sensitive silver halide emulsion layer so that it serves as a filter layer which transmitts only light of the desired wavelength.

An antihalation layer is provided between the light-sensitive emulsion layer and the support or between the back side of the support and the antihalation layer to absorb harmful light reflected by the interface between the emulsion layer and the support or by the back side of the support for the purpose of improving sharpness of images.

Further, for the purpose of improving sharpness of images, the silver halide emulsion layer may comprise a dye capable of absorbing light of a wavelength range to which silver halide is sensitive to inhibit irradiation.

In particular, a silver halide photographic material for use in the photomechanical process, more particularly daylight light-sensitive material, may comprise a dye which absorbs ultraviolet light or visible light in a light-sensitive layer or a layer provided between the light source and the light-sensitive layer to improve its safety to safelight.

Moreover, X-ray sensitive materials may comprise a colored layer for improving sharpness as a crossover cut filter for eliminating crossover light.

These layers which are to be colored are often made of a hydrophilic colloid. Therefore, in order to be colored, these layers normally comprise a dye incorporated therein. Such a dye is required to satisfy the following conditions:

(1) The dye should exhibit a proper spectral absorption depending on the purpose of use;

(2) The dye should be photochemically inert. In other words, the dye should have no chemically adverse effects on the properties of the silver halide photographic emulsion layer, e.g., sensitivity drop, fading of latent images and photographic fog;

(3) The dye should be decolored but dissolved away upon photographic processing so that harmful colors are not left on the photographic light-sensitive material after processing; and (4) The dye should exhibit an excellent age stability and should not deteriorate in the coating solution or silver halide photographic material.

In order to find dyes which meet these requirements, many efforts have been made. Examples of dyes thus proposed include pyrazolone oxonol dyes as described in British Patent 506,385, barbituric oxonol dyes as described in U.S. Pat. No. 3,247,127, azo dyes as described in U.S. Pat. No. 2,390,707, styryl dyes as described in U.S. Pat. No. 2,255,077, hemioxonol dyes as described in British Patent 584,609, melocyanine dyes as described in U.S. Pat. No. 2,493,747, cyanine dyes as described in U.S. Pat. No. 2,843,486, and methylenic benzylidene dyes as described in U.S. Pat. No. 4,420,555.

If the layer containing these dyes serves as a filter layer or an antihalation layer, it is necessary that the layer be selectively colored without substantially coloring the other layers. This is because that if the other layers are also substantially colored, it not only causes a harmful spectral effect on the other layers but also eliminates the effects provided by the filter layer or antihalation layer. Further, when a dye which has been incorporated in a specific layer for the purpose of inhibiting irradiation diffuses into and colors other layers, problems similar to those described above occur.

As an approach for solving these problems, an approach is known which comprises localizing an acidic dye containing a sulfo group or a carboxyl group in a specific layer with a mordant.

Examples of such a known mordant include ethylenically unsaturated compound polymers as described in British Patent 685,475, reaction products of polyvinyl alkyl ketone and amino guanidine as described in British Patent 850,281, and vinyl pyridine polymers and vinyl pyridinium cation polymers as described in U.S. Pat. Nos. 2,548,564, 2,484,430, 3,148,061, and 3,756,814. In order to effectively mordant the above mentioned acidic dye, a cationic mordant containing secondary and tertiary amino groups, nitrogen-containing heterocyclic groups and quaternary cation groups in a polymer is used.

However, the mordanting process is disadvantageous in that when the layer in which a dye is incorporated comes into contact with other hydrophilic colloidal layers in a wet state, the dye often partially diffuses into the other hydrophilic layers. Of course, the dye diffusion depends on the chemical structure of the mordant. The dye diffusion also depends on the chemical structure of the dye used.

If a high molecular weight mordant is used, remaining color remaining can easily occur on the light-sensitive material after photographic processing, particularly shortened photographic processing. This occurs because the mordant exhibits a very weak bond strength but does have some bond strength, with the dye in an alkaline solution, such as the developer; therefore, the dye or reversible decolored products partially remain in the layer containing the mordant.

However, these cationic mordants may undergo static interaction with gelatin which is often used as a hydrophilic colloid and a surface active agent containing an alcoholate group, a carboxylate group, a sulfonate group or a sulfate group which is normally used as coating aid to prevent deterioration of coating properties.

These cationic mordants may also cause deterioration of desilvering properties and a sensitivity drop in the layers adjacent to the mordant-containing layer in a color light-sensitive material.

With such a mordant, very often the above mentioned dye diffuses into other layers. Therefore, it has been proposed to use such a mordant in a larger amount to inhibit diffusion. However, even with this approach, diffusion cannot be completely eliminated. Further, with this approach, the layer in which the mordant is incorporated needs to be thicker, causing deterioration of sharpness.

In the processing of light-sensitive material for printing process, reduction with a reducer is normally effected to adjust density and gradation. However, since the reducer contains a water-soluble iron complex as a reducing agent, the above mentioned cationic mordant undergoes static bonding with the iron complex to cause yellow stain with the iron complex.

These disadvantages can be eliminated by the use of a dye as described in JP-A-63-280246 (the term "JP-A" as used herein means an "unexamined published Japanese patent application"). However, this approach is disadvantageous in that decolorability leaves much to be desired in low pH rapid processing.

Further, in a color light-sensitive material, colloidal silver has previously been used for the purpose of inhibiting absorption of yellow light and halation. However, the use of colloidal silver is disadvantageous in that fog in the light-sensitive silver halide emulsion layer adjacent to the colloidal silver layer becomes more remarkable. Elimination of these difficulties has been sought.

Other approaches for retaining a dye in a specific layer in the photographic light-sensitive material include known approaches which comprise allowing a dye to be present in the form of disperse solid as disclosed in JP-A-56-12639, 55-155350, 55-155351, 52-92716, 63-197943, 63-27838, and 64-40827, European Patents 0015601B1 and 0276566A1, and International Patent Application Disclosure 88/04794.

However, these approaches are obviously characterized absorption spectrum of disperse solid-coated material such that the absorption peak is shifted as compared to that of the same dye in the form of solution or in a form dissociated at pH 10, widening the half band width (HBW).

The widening of the half band width may be suitable for a filter for use where exposure is required in a wide wavelength range but is generally disadvantageous since it reduces the value of absorbance. Further, an excessively wide half band width is rather disadvantageous in a multilayer silver halide photographic material when a filter for shutting off light of undesired wavelength in the spectral sensitivity range of a lower layer such as yellow filter and magenta filter is used or when a disperse solid dye is used as safelight filter layer as described in JP-A-2-110453. Moreover, if the dye is incorporated in an antihalation layer in a light-sensitive layer having a very narrow spectral sensitivity range or if the dye is incorporated in an antihalation layer for exposure to light of a very narrow wavelength range, the low absorbance leads to the requirement of a large coated amount of dye, causing many disadvantages such as deterioration of decolorability, increase in thickness and cost rise.

SUMMARY OF THE INVENTION

It is therefore an object of the present invention to provide a silver halide photographic material comprising a hydrophilic colloidal layer colored with a dye which can be irreversibly decolored by photographic processing and has no adverse effect on the photographic properties of photographic emulsions.

It is another object of the present invention to provide a silver halide photographic material wherein only desired hydrophilic colloidal layers can be sufficiently selectively colored with dyes and these hydrophilic colloidal layers exhibit an excellent decolorability by photographic processing (particularly low pH rapid processing).

It is a further object of the present invention to provide a novel method for fixing a dye having a high absorbance and a sharp absorption.

It is a still further object of the present invention to provide a silver halide photographic material comprising at least one layer colored with a dye which inhibits interaction between gelatin and a coating aid and exhibits an improved coatability.

These and other objects and advantages of the present invention will become more apparent from the following detailed description and examples, and are accomplished by a silver halide photographic material comprising on a support at least one silver halide emulsion layer, wherein said emulsion layer or other hydrophilic colloidal layers comprise at least one compound represented by formula (I):

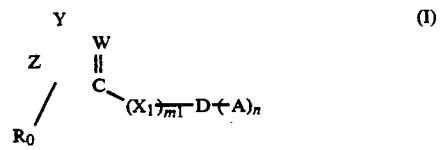

wherein W represents =N— or

in which $R_1$ represents a hydrogen atom or a substituent; $R_0$ represents an alkyl group containing 10 or more carbon atoms or an aromatic group containing 12 or more carbon atoms; Z represents an atomic group which can form a heterocyclic group or a carbon ring; Y represents

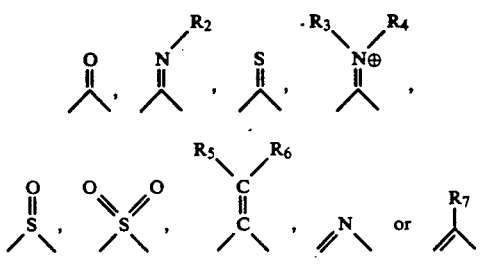

wherein $R_2$, $R_3$, $R_4$, $R_5$, $R_6$ and $R_7$ each represents a hydrogen atom or a substituent; $X_1$ represents a divalent group connected to carbon atom via a hetero atom contained therein; D represents a photographic dye portion connected to $X_1$ via a hetero atom contained therein; A represents a water-solubilizing group; $m_1$ represents an integer 0 or 1; and n represents an integer 2 or more.

DETAILED DESCRIPTION OF THE INVENTION

JP-A-63-280246 discloses a compound containing two sulfonates and a compound containing two carboxylates as compounds analogous to the compound of the present invention. However, these compounds are disadvantageous since the alkyl group or aromatic group as the substituent connected to an elimination reaction nucleus containing a release group having a dye portion has a small number of carbon atoms. Therefore, these compounds may not be sufficiently fixed in a coat film or may increase its thickening or deteriorate its stability when mixed with gelatin. These compounds are also disadvantageous since the activity of the reaction nucleus itself is low, the compounds may not be sufficiently decolored.

The compound represented by formula (I) undergoes addition of a nucleating agent in the processing solution (e.g., $OH^-$ ion, $SO_3^{2-}$ ion, hydroxylamine) to an unsaturated bond upon photographic processing (e.g., development, bleach, fixing, blix (bleaching-fixing)) to enable elimination of $D(A)_n$ which is defined above and further defined below.

Methods for blocking the active group utilizing the addition of a nucleating agent to an unsaturated bond include those described in JP-A-59-201057, 61-43739, 61-95347, and 1-245255.

Formula (I) will be further described hereinafter.

The alkyl group containing 10 or more carbon atoms represented by $R_0$ in Formula (I) is a straight-chain, branched or cyclic alkyl group.

The straight-chain or branched alkyl group may be cyclized so that it forms a saturated heterocyclic group containing one or more hetero atoms. The alkyl group may be substituted by substituents. Preferred examples of such substituents include an aryl group, an aryloxy group, an alkoxy group, an alkoxycarbonyl group, an amino group, a ureide group, a urethane group, a sulfoxy group, a sulfonamide group, and a carbonamide group.

In formula (I), the aromatic group containing 12 or more carbon atoms represented by $R_0$ is a monocyclic or bicyclic aryl or unsaturated heterocyclic group. The unsaturated heterocyclic group may be condensed to a monocyclic or bicyclic aryl groups to form a heteroaryl group such as a benzene ring, a naphthalene ring, a pyridine ring, a pyrimidine ring, an imidazole ring, a pyrazole ring, a quinoline ring, an isoquinoline ring and a benzimidazole ring. Particularly preferred among these groups are those containing benzene ring.

The monocyclic or bicyclic aryl group or unsaturated heterocyclic group represented by $R_0$ may be substituted by substituents. Typical examples of such substituents include an alkyl group, an aralkyl group, an alkenyl group, an alkinyl group, an alkoxy group, an aryl group, a substituted amino group, a ureide group, a urethane group, an aryloxy group, a sulfamoyl group, a carbamoyl group, an alkylthio group, an arylthio group, an alkylsulfonyl group, an arylsulfonyl group, an alkylsulfinyl group, an arylsulfinyl group, a hydroxyl group, a halogen atom, a cyano group, a sulfo group, an aryloxycarbonyl group, an acyl group, an alkoxycarbonyl group, an acyloxy group, a carbonamide group, a sulfonamide group, a carboxyl group, a phosphoric amide group, a diacylamino group, and a imide group. Preferred examples of such substituents include a straight-chain, branched or cyclic alkyl group (preferably containing 1 to 20 carbon atoms), an aralkyl group (preferably monocyclic or bicyclic aralkyl group containing a $C_{1-3}$ alkyl portion), an alkoxy group (preferably containing 1 to 20 carbon atoms), a substituted amino group (preferably an amino group substituted by $C_{1-20}$ alkyl group), an acylamino group (preferably containing 2 to 30 carbon atoms), a sulfonamide group (preferably 1 to 30 carbon atoms), and a ureide group (preferably containing 1 to 30 carbon atoms), and a phosphoric amide group (preferably 1 to 30 carbon atoms).

Particularly preferred groups represented by $R_0$ include an alkyl group containing 10 to 30 carbon atoms and an aromatic group containing 12 to 30 carbon atoms.

$R_1$ represents a hydrogen atom, a halogen atom (e.g., fluorine, chlorine, bromine), an alkyl group (preferably containing 1 to 20 carbon atoms), an aryl group (preferably containing 6 to 20 carbon atoms), an alkoxy group (preferably containing 1 to 20 carbon atoms), an aryloxy group (preferably containing 6 to 20 carbon atoms), an alkylthio group (preferably containing 1 to 20 carbon atoms), an arylthio group (preferably 6 to 20 carbon atoms), an acyl group (preferably containing 2 to 20 carbon atoms), an acylamino group (preferably a $C_{1-20}$ alkanoylamino group or a $C_{6-20}$ benzoylamino group), a nitro group, a cyano group, an oxycarbonyl group (preferably a $C_{1-20}$ alkoxycarbonyl group or a $C_{6-20}$ aryloxycarbonyl group), a hydroxyl group, a carboxyl group, a sulfo group, a ureide group (preferably a $C_{1-20}$ alkylureide group or a $C_{6-20}$ arylureide group), a sulfonamide group (preferably a $C_{1-20}$ alkylsulfonamide group or a $C_{6-20}$ arylsulfonamide group), a sulfamoyl group (preferably a $C_{1-20}$ alkylsulfamoyl group or a $C_{6-20}$ arylsulfamoyl group), a carbamoyl group (preferably a $C_{1-20}$ alkylcarbamoyl group or a $C_{6-20}$ arylcarbamoyl group), an acyloxy group (preferably containing 1 to 20 carbon atoms), an amino group (a unsubstituted amino group, preferably a secondary or tertiary amino group substituted by a $C_{1-20}$ alkyl group or a $C_{6-20}$ aryl group), a carbonic ester group (preferably a $C_{1-20}$ alkylcarbonic ester group or a $C_{6-20}$ arylcarbonic ester group), a sulfon group (preferably a $C_{1-20}$ alkylsulfon group or a $C_{6-20}$ arylsulfon group), or a sulfinyl group (preferably a $C_{1-20}$ alkylsulfinyl group or a $C_{6-20}$ arylsulfinyl group).

These groups each may contain one or more substituents. Specific examples of such substituents include those described with reference to $R_0$.

Preferred among these substituents represented by $R_1$ are a hydrogen atom, a halogen atom, an arylthio group, an oxycarbonyl group, a carbamoyl group, an acyl group, a sulfonyl group, a sulfamoyl group, a sulfinyl group, a cyano group, and a nitro group.

Y represents

Y represents

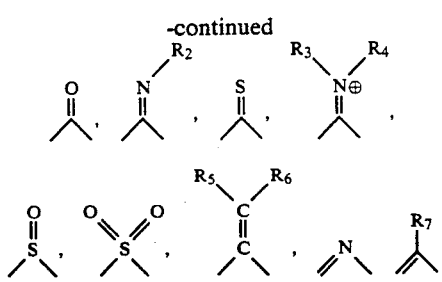

wherein $R_2$, $R_3$, $R_4$, $R_5$, $R_6$ and $R_7$ may same or different and each represents a hydrogen atom or a substituent. Specific examples of substituents include a halogen atom (e.g., fluorine, chlorine, bromine), an alkyl group (preferably containing 1 to 20 carbon atoms), an alkenyl group (preferably containing 2 to 20 carbon atoms), an aryl group (preferably containing 6 to 20 carbon atoms), an alkoxy group (preferably containing 1 to 20 carbon atoms), an aryloxy group (preferably 6 to 20 carbon atoms), an acyloxy group (preferably 2 to 20 carbon atoms), an amino group (including an unsubstituted amino group or, preferably, a secondary or tertiary amino group substituted by a $C_{1-20}$ alkyl group or a $C_{6-20}$ aryl group), a carbonamide group (preferably a $C_{1-20}$ alkylcarbonamide group or a $C_{6-20}$ arylcarbonamide group), a ureide group (preferably a $C_{1-20}$ alkylureide group or a $C_{6-20}$ arylureide group), an oxycarbonyl group (preferably a $C_{1-20}$ alkyloxycarbonyl group or a $C_{6-20}$ aryloxycarbonyl group), a carbamoyl group (preferably a $C_{1-20}$ alkylcarbamoyl group or a $C_{6-20}$ arylcarbamoyl group), an acyl group (preferably a $C_{1-20}$ alkylcarbonyl group or a $C_{6-20}$ arylcarbonyl group), a sulfonyl group (preferably a $C_{1-20}$ alkylsulfonyl group or a $C_{6-20}$ arylsulfonyl group), a sulfinyl group (preferably a $C_{1-20}$ alkylsulfinyl group or a $C_{6-20}$ arylsulfinyl group), a sulfamoyl group (preferably a $C_{1-20}$ alkylsulfamoyl group or a $C_{6-20}$ arylsulfamoyl group), a cyano group, and a nitro group. Among these substituents, those preferable for $R_4$ and $R_5$ are an oxycarbonyl group, a carbamoyl group, an acyl group, a sulfonyl group, a sulfamoyl group, a sulfinyl group, a cyano group, and a nitro group. These substituents each may contain one or more substituents. When there are contained two or more substituents, they may be the same or different. Specific examples of such substituents include those described with reference to $R_0$.

Z represents an atomic group which forms a heterocyclic group or a carbon ring. Examples of the carbon ring or the heterocyclic group which can be formed include a 5-membered, 6-membered or 7-membered carbon ring, and a 5-membered, 6-membered or 7-membered heterocyclic group containing one or more nitrogen, oxygen or sulfur atoms. These carbon rings or heterocyclic groups may be condensed at a proper position to form a condensed ring.

Specific examples of the carbon ring or the heterocyclic group represented by Z include cyclopentenone, cyclohexenone, cycloheptenone, benzocycloheptenone, benzocyclopentenone, benzocyclohexenone, 4-pyridone, 4-quinolone, quinone-2-pyrone, 4-pyrone, 1-thio-2-pyrone, 1-thio-4-pyrone, coumarine, chromone, uracil, cyclohexanone, cycloheptanone, benzocycloheptanone, benzocyclopentanone, benzocyclohexanone, 4-tetrahydropyridone, 4-dihydroquinolone, 4-tetrahydropyrone, imidazoline, thiazoline, oxazoline, pyrrole, oxazole, thiazole, imidazole, triazole, tetrazole, pyridine, pyrimidine, pyrazine, pyridazine, triazine, condensed ring formed by condensation of heterocyclic groups at a proper position, such as quinoline, isoquinoline, phthalazine, quinazoline, quinosaline, benzothiazole, benzoxazole, benzoimidazole, naphthyridine, thiazolo[4,5-d]pyrimidine, 4H-pyrido[1,2-a]pyrimidine, imidazo[1,2-a]pyridine, pyrrolo[1,2-a]pyrimidine, 1H-pyrrolo[2,3-b]pyridine, 1H-pyrrolo[3,2-b]pyridine, 6H-pyrrolo[3,4-b]pyridine, benzoimidazole, triazaindenes (e.g., pyrido[3,4-d]pyridazine, pyrido[3,4-d]pyrimidine, imidazo[1,5-a]pyrimidine, pyrazolo[1,5-a]pyrimidine, 1H-imidazo[4,5-b]pyridine, 7H-pyrrolo[2,3-d]pyrimidine), tetrazaindenes (e.g., pteridine, 4H-imidazo[1,2-b][1,2,4]triazole, imidazo[4,5-d]imidazole, 1H-1,2,4-triazolo[4,3-b]pyridazine, 1,2,4-triazolo[1,5-a]pyrimidine, imidazo[1,2-a]-1,3,5-triazine, pyrazolo[1,5-a]-1,3,5-triazine, 7H-purine, 9H-purine, 1H-pyrazolo[3,4-d]pyrimidine) and pentazaindenes (e.g., [1,2,4]triazolo[1,5-a][1,3,5]triazine, 1,2,4-triazolo[3,4-f][1,2,4]triazine, 1H-1,2,3-triazolo[4,5-d]pyrimidine), and

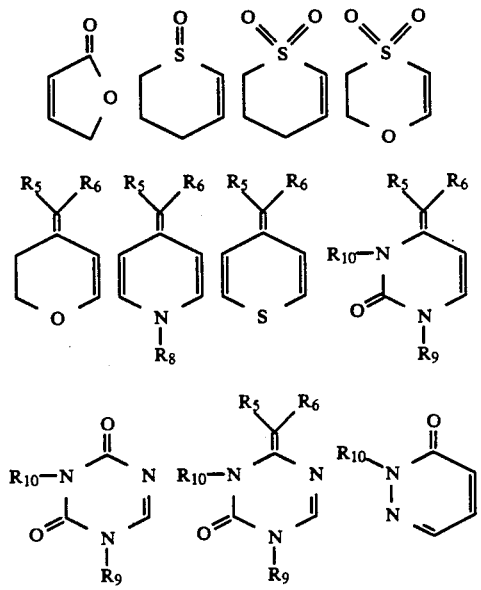

(in which $R_5$ and $R_6$ are as defined in formula (I); and $R_8$, $R_9$ and $R_{10}$ each represents a hydrogen atom, an alkyl group, an alkenyl group, an aryl group, an aralkyl group or an acyl group).

Preferred among the carbon rings represented by Z are cyclopentenones, cyclohexenones, cyclopentanones, cyclohexanones and quinones. Preferred among the heterocyclic groups are coumarine, chromone, uracils and nitrogen-containing aromatic heterocyclic groups.

Preferred among the nitrogen-containing aromatic heterocyclic groups are pyridine, pyrimidine, pyrazine, triazine, quinoline, quinazoline, quinoxaline, triazaindenes, tetrazaindenes, and pentazaindenes. Particularly preferred among these groups are triazaindenes, tetrazaindenes, and pentazaindenes.

The carbon rings or heterocyclic groups each may contain one or more substituents. When two or more substituents are present, they may be the same or different. Specific examples of such substituents include those described with reference to $R_0$.

X represents a divalent linking group connected to carbon atom via a hetero atom contained therein. The divalent linking group can rapidly release $D(A)_n$, defined above, after being cleaved as $X_1—D(A)_n$ upon processing. In formula (I), $m_1$ represents an integer 0 or 1.

Examples of the divalent linking group represented by $X_1$ include those which undergo an intramolecular ring-closure reaction to release $D—(A)_n$ as described in JP-A-54-145135 (corresponding to British Patent 2,010,818A), U.S. Pat. Nos. 4,248,962 and 4,409,323, and British Patent 2,096,783, those which undergo an intramolecular electron migration to release $D—(A)_n$ as described in British Patent 2,072,363, and JP-A-57-154234, those which release $D—(A)_n$ with the elimination of carbon dioxide gas as described in JP-A-57-179842, and those which release $D—(A)_n$ with the elimination of formalin as described in JP-A-59-93422. Typical examples of $X_1$— will be set forth below in a structural formula with $D—(A)_n$.

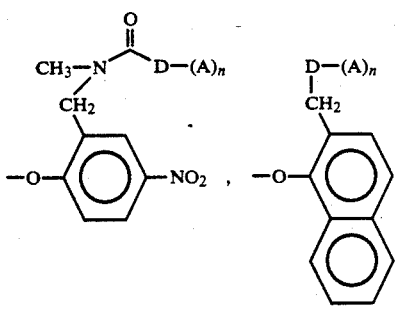

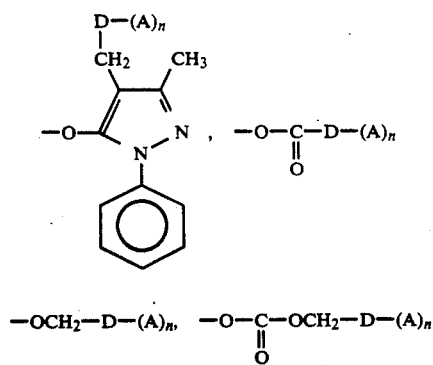

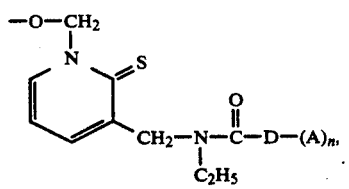

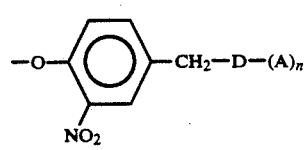

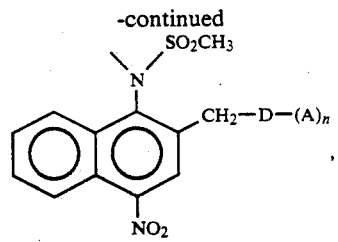

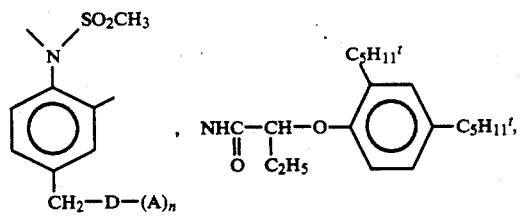

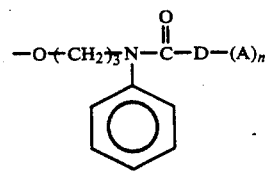

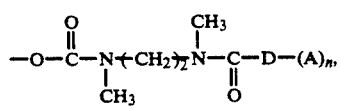

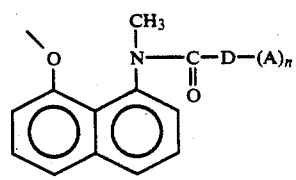

D represents a photographic dye portion. The photographic dye portion is a dye which cannot selectively color the layer in which it is incorporated by itself and which undergoes a reaction such as discoloration and an elution from the light-sensitive material upon photographic processing (e.g., development, bleach, fixing, rinse) so that contamination such as stain and residual color is not substantially left on the light-sensitive material.

In other words, in a blocked state as shown in formula (I), the compound of the present invention remains nondiffusible and can selectively remain in the layer in which it is incorporated, whereas the dye portion represented by $D—(A)_n$ is diffusible.

Examples of such a dye include compounds as described in "Kokino Photochemicals—Kozo Kino to Oyo Tenbo—(High Function Photochemicals—Structural Function and Scope of Application—)", CMC, 1986, pp. 197–211.

Specific examples of the dye in the photographic dye portion include arylidene dye, styryl dye, butadiene dye, oxonol dye, cyanine dye, melocyanine dye, hemicyanine dye, diarylmethane dye, triarylmethane dye, azomethine dye, azo dye, metal chelate dye, anthraquinone dye, stilbene dye, chalcone dye, indophenol dye, indoaniline dye, and coumarine dye.

In view of their absorption wavelength ranges, these dyes include dyes which mainly absorb light of a wavelength range shorter than 400 nm (UV absorption dye)

and dyes which mainly absorb light of a wavelength range longer than 700 nm (infrared dye) in addition to dyes which absorb visible light range. Specific examples of dyes normally used as UV dyes include arylidene dye, butadiene dye, and coumarine dye. Specific examples of dyes normally used as infrared dyes include oxonol dye, cyanine dye, melocyanine dye, hemicyanine dye, metal chelate dye, triarylmethane dye, anthraquinone dye, and indoaniline dye. The photographic dye portion represented by D may be connected to carbon atom via a hetero atom ($m_1=0$) or $X_1$ ($m_1=1$).

A represents a water-solublizing group. Examples of the water-solubilizing group represented by A include —COOM, —SO$_3$M, —OSO$_3$M,

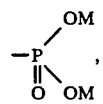

and —OH in which M represents a hydrogen atom, an alkaline metal atom (e.g., Na, K), quaternary ammonium or quaternary phosphonium.

The plurality of A's may be the same or different. In formula (I), n represents an integer 2 or more.

Specific examples of the compound represented by formula (I) used in the present invention will be set forth below, but the present invention should not be construed as being limited thereto.

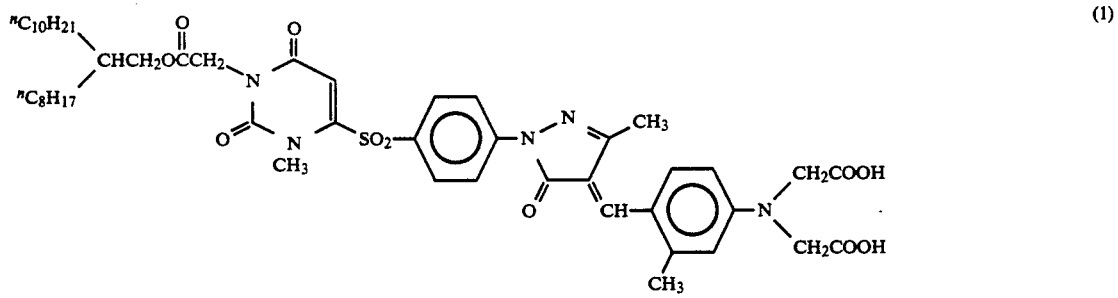

(1)

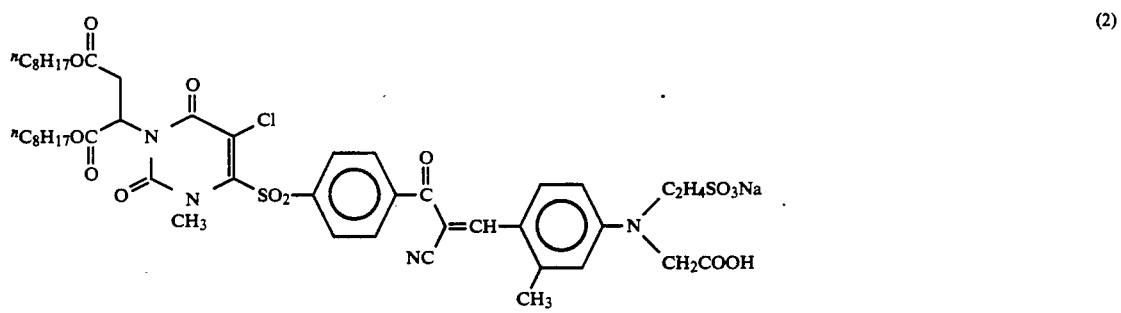

(2)

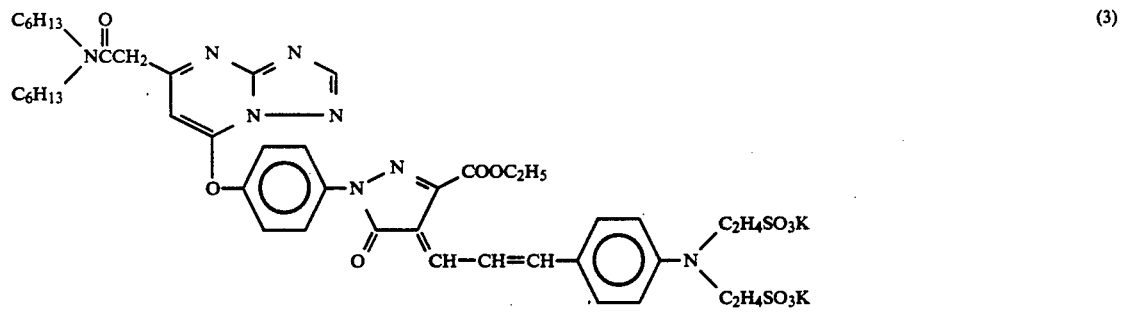

(3)

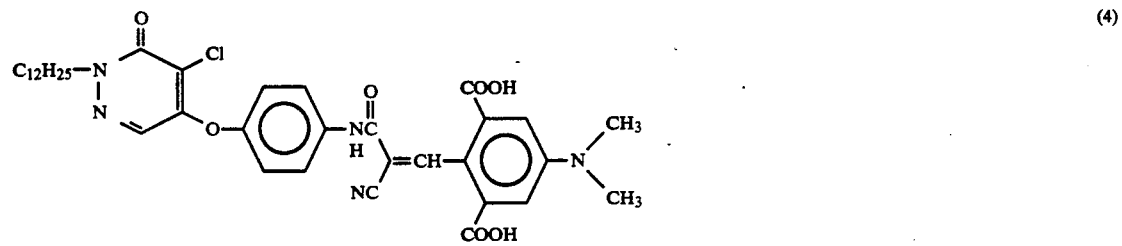

(4)

-continued
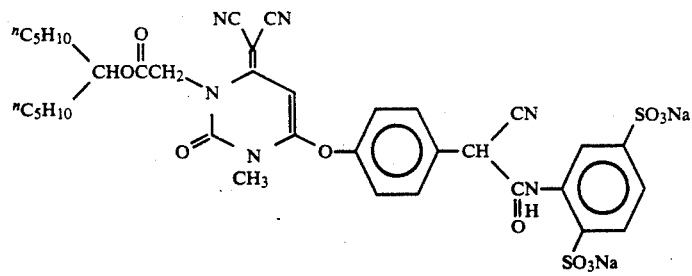 (5)
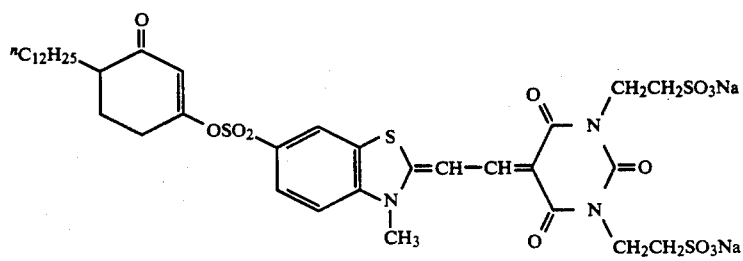 (6)
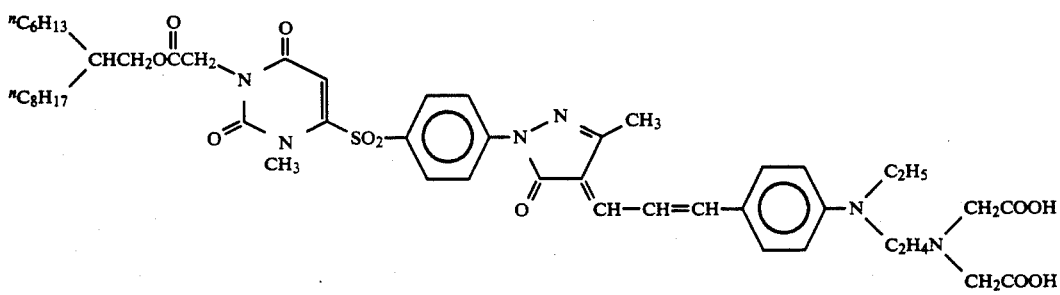 (7)
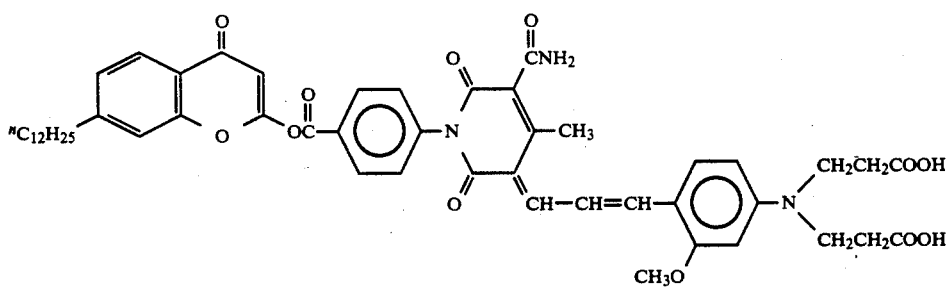 (8)
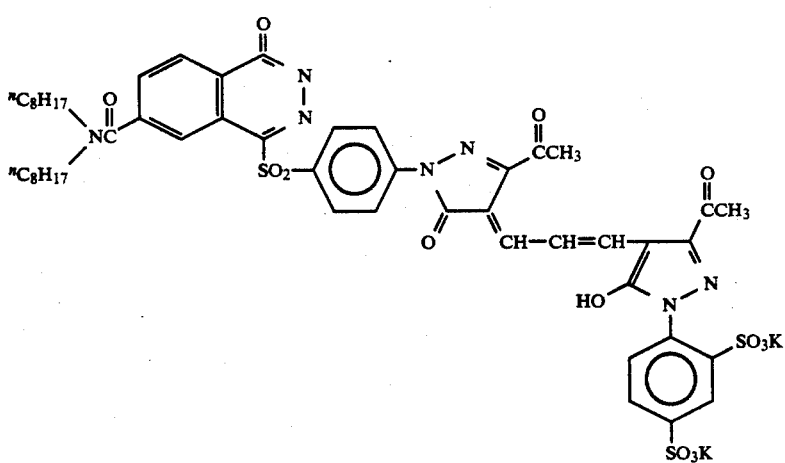 (9)

-continued
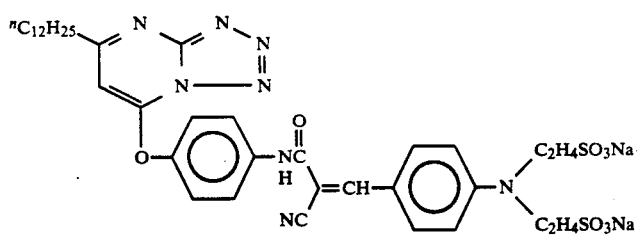 (10)
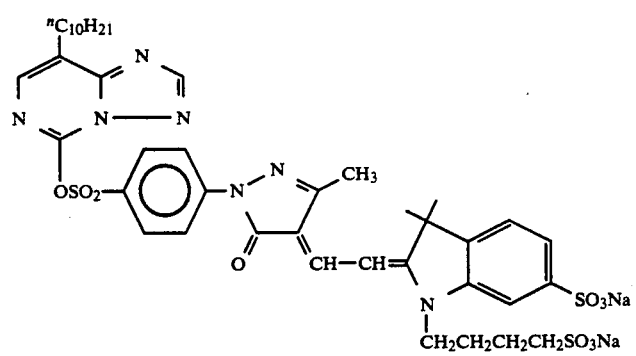 (11)
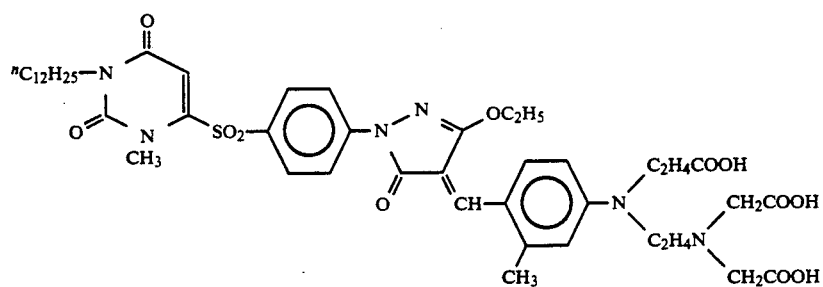 (12)
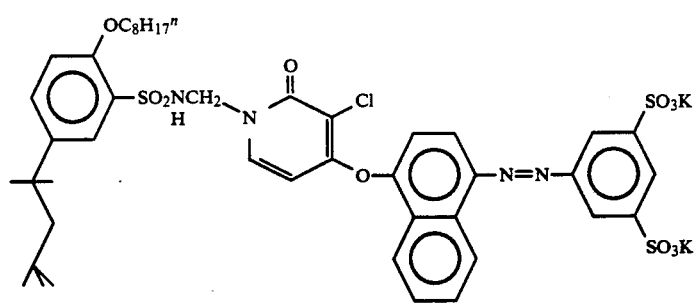 (13)
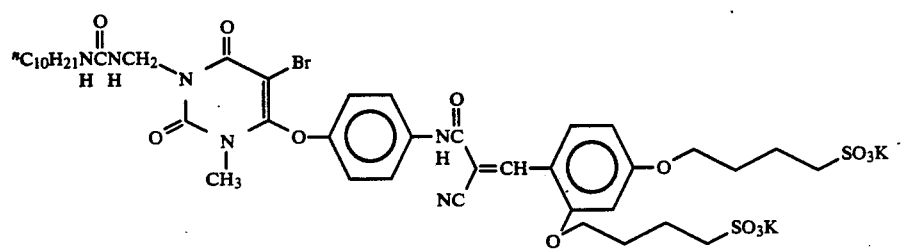 (14)

-continued

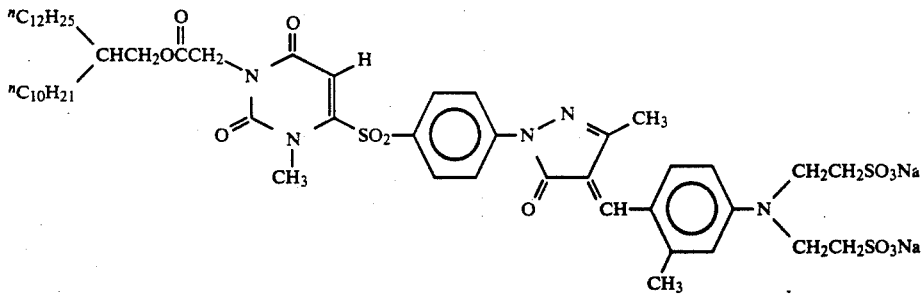
(15)

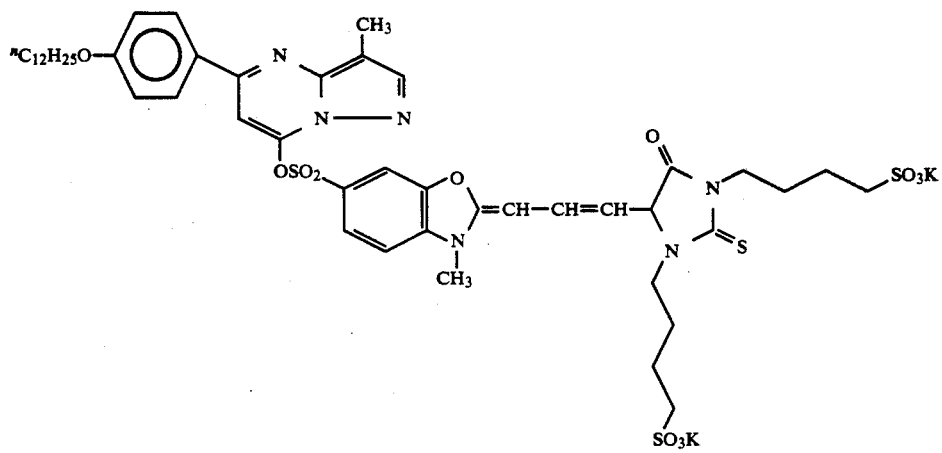
(16)

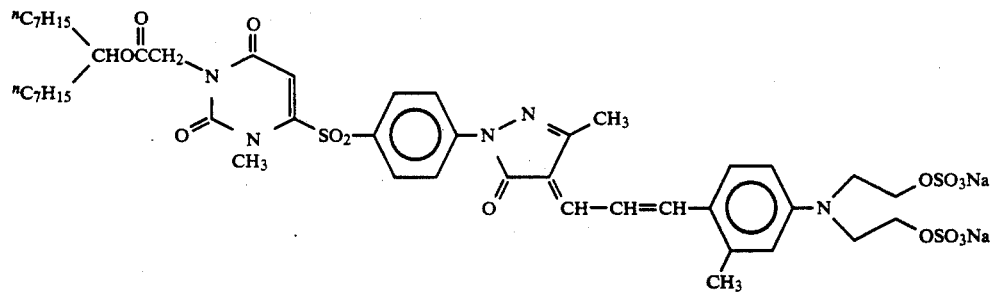
(17)

A description of the synthesis of compound (1) is shown below.

SYNTHESIS EXAMPLE 1

Synthesis of Exemplary Compound (1)

Synthesis of Block Group Portion 20 g of 2-decyl-2-octylethanol, 20 g of bromoacetic acid, and 2.5 g of p-toluenesulfonic acid were added to 150 ml of toluene. The material was then subjected to aezotropic dehydration for 1.5 hours. After being allowed to cool, the material was extracted with water. The organic phase was dried with MgSO4. Toluene was removed under reduced pressure to obtain 46 g of ester 2-decyl-2-octylethylbromoacetate.

15 g of 6-chloro-1-methyluracil was suspended in 50 ml of acetonitrile. 15 ml of DBU was added to the suspension at room temperature to prepare a uniform solution. The solution was stirred for 15 minutes. 40 g of ester 2-decyl-2-octylethylbromoacetate was added dropwise to the material at room temperature. The mixture was stirred at room temperature for 2.5 hours. Dust was removed from the material by filtration. Acetonitrile was removed from the material under reduced pressure. Ethyl acetate was added to the residue. DBU and HBr, thus deposited, were removed from the material. The filtrate was washed with dilute hydrochloric acid. The material was dried with MgSO4. Ethyl acetate was removed under reduced pressure. The residue was purified through silica gel chromatography to obtain 31 g of 6-chloro-1-methyl-3-(2-decyl-2-octyl-ethoxycarbomethyluracilin the form of oil.

Synthesis of Dye Portion 400 g of 4-(3-methyl-5-oxo-2-pyrazoline-1-yl)benzenesulfonic acid was suspended in 1.5 l of acetonitrile. 480 ml of triethylamine was added dropwise to the suspension at room temperature to prepare a uniform solution. After the reaction solution was cooled with ice, 300 g of p-toluenesulfonyl chloride was gradually added to the reaction solution. After the dropwise addition was completed, the reaction solution was stirred for 1 hour under cooling with ice and then for 1 hour at room temperature. The resulting triethylamine hydrochloride was then filtered off. The filtrate was concentrated. A mixture of n-hexane and ethyl acetate was added to the residue. The resulting crystal was filtered off, and then dried to obtain 785 g of triethylamine 4-[3-methyl-5-(4-methylphenylsulfoxy)-2-pyrazol-1-yl]benzenesulfonate.

835 g of triethylamine 4-[3-methyl-5-(4-methylphenylsulfoxy)-2-pyrazol-1-yl]benzenesulfonate thus obtained was dissolved in 1.5 l of acetonitrile without being purified. After being cooled with ice, 400 ml of phosphorus oxychloride was added to the reaction solution. The reaction solution was then stirred for 10 minutes. 500 ml of N,N-dimethylacetamide was slowly added dropwise to the reaction solution. The reaction solution was then stirred under cooling with ice for 1 hour. The reaction solution was then poured into 10 kg of ice. The reaction solution was then extracted with 10 l of ethyl acetate. The ethyl acetate phase thus extracted was dried. Ethyl acetate was removed from the ethyl acetate phase under reduced pressure. The resulting crystal was washed with acetonitrile, and then dried to obtain 580 g of 4-[3- methyl-5-(4-methylphenylsulfoxy)-2-pyrazol-1-yl]benzenesulfonyl chloride in the form of light yellow crystal (m.p.: 103° C.).

500 g of 4-[3-methyl-5-(4-methylphenylsulfoxy)-2-pyrazol-1-yl]benzenesulfonyl chloride was added to a solution of 427 g of sodium sulfite anydride in 2 l of water. The reaction solution was heated to a temperature of 50° to 60° C. A solution of 72 g of sodium hydroxide in 500 ml of water was added dropwise to the reaction solution in 1 hour. The reaction solution was then stirred for 1 hour to prepare a nearly uniform solution. The reaction solution was then allowed to cool. The insoluble matters were removed from the reaction solution by filtration. The filtrate was cooled with ice. A solution of 93 ml of concentrated sulfuric acid in 200 g of water was added dropwise to the filtrate in 30 minutes so that the pH value of the reaction solution was adjusted to 1 or less. The reaction solution was then stirred under cooling with ice for 1 hour. The resulting crystal was filtered off, washed with water several times to remove inorganic contents therefrom, and then dried to obtain 260 g of 4-[3-methyl-5-oxo-2-pyrazoline-1- yl]benzenesulfinic acid. The product was then added to 180 g of 28 % sodium methoxide and 2 l of methanol without being purified. Dissolution was completely made in 30 minutes. Dust was removed from the material by filtration. Methanol was removed from the material under reduced pressure. The material was washed with acetonitrile, filtered off, and then dried to obtain 240 g of sodium 4-[3-methyl-5-oxo-2-pyrazoline-1-yl]benzenesulfinate in the form of white crystal (m.p. 250° C. or higher).

4 ml of acetic acid was added to a solution of 27 g of 6-chloro-1-methyl-3-(2-decyl-2-octylethoxy) carbomethyluracil and 16 g of sodium 4-(3-methyl-5-oxo-2-pyrazoline-1-yl) benzenesulfinate in 160 ml of dimethylacetylamide. The mixture was stirred at a temperature of 60° C. for 3 hours. After being allowed to cool, saturated brine was added to the material. The material was extracted with 500 ml of ethyl acetate twice, and then washed with water. The resulting organic phase was dried with MgSO$_4$. Ethyl acetate was removed from the material under reduced pressure. The residue was purified through silica gel chromatorgraphy to obtain 23 g of the intermediate 1 in the form of oil. The reaction to obtain intermediate 1 followed by the reaction to obtain compound 1 is shown below.

0.5 g of ammonium acetate was added to 3.4 g of the intermediate 1, 1.25 g of aldehyde and 50 ml of ethanol. The mixture was heated under reflux for 6 hours. After being allowed to cool, the resulting crystal was filtered off, and then dried under reduced pressure to obtain 3.1 g of an exemplary compound (1).

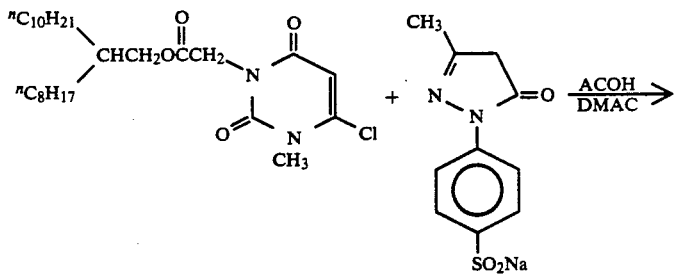

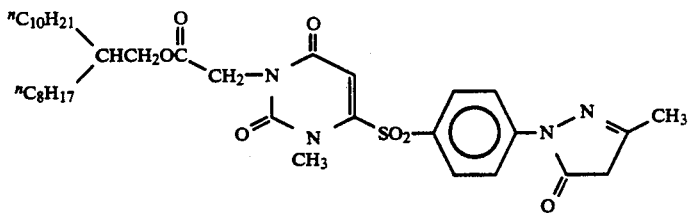

intermediate 1

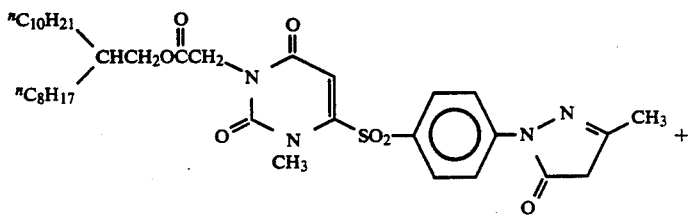

intermediate 1

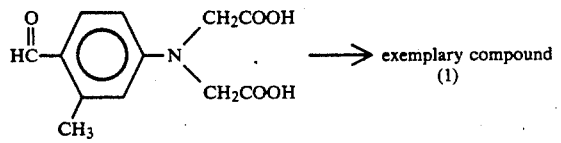 → exemplary compound (1)

The rate at which D—(A)$_n$ is released from the compound of the present invention can be broadly controlled by properly adjusting pH as well as by a proper use of a nucleophilic substance such as sulfite ion, hydroxylamine, thiosulfuric ion, metabisulfuric ion, hydroxamic acid and analogous compounds as described in JP-A-59-198453, oxim compounds as described in JP-A-60-35729, and dihydroxybenzene developing agent, 1-phenyl-3-pyrazolidone developing agent and p-aminophenolic developing agent, as described later.

The amount of such a nucleophilic substance to be added is normally in the range of 1 to $10^8$ times, preferably $10^2$ to $10^6$ times the molar amount of the compound of the present invention.

The compound of formula (I) to be used in the present invention may be incorporated in the layer in a desired amount depending on the purpose. The compound of the general formula (I) may be preferably used in such an amount that the photographic material gives an optical density of 0.05 to 3.0. In particular, the amount of the dye to be used depends on the type of the dye and is normally used in the range of $10^{-3}$ g/m$^2$ to 3.0 g/m$^2$, preferably $10^{-3}$ g/m$^2$ to 1.0 g/m$^2$.

The compound of formula (I) of the present invention may be incorporated in the hydrophilic colloidal layer by various known methods.

For example, the compound of formula (I) may be 1) dissolved in a proper solvent such as alcohol (e.g., methanol, ethanol, propanol), acetone, methyl ethyl ketone, methyl cellosolve, dimethyl formamide, cyclohexanone and ethyl acetate, 2) dissolved or dispersed in gelatin, and then 3) incorporated in the hydrophilic colloidal layer or may be 1) dissolved in a high boiling oil, and then 2) incorporated in the hydrophilic colloidal layer in the form of fine oil emulsion dispersion. The oil used can be a known oil such as tricresyl phosphate, diethyl phthalate, dibutyl phthalate and triphenyl phosphate.

Alternatively, the compound of formula (I) may be 1) dispersed in an aqueous medium in the absence or presence of a known emulsifier or surface active agent by agitation, ultrasonic apparatus or various mills, and then 2) incorporated in the hydrophilic colloidal layer. The emulsifier or surface active agent which may be used include ordinary anionic, nonionic, cationic or betainic emulsifier or surface active agent. Anionic, nonionic and betainic emulsifiers or surface active agents are particularly preferred.

The compound of the present invention may be incorporated in any layers depending on the purpose. In particular, the compound of the present invention may be incorporated in at least of hydrophilic colloidal layers such as a subbing layer, an antihalation layer provided between a silver halide emulsion layer and the support, a silver halide emulsion layer, an interlayer, a protective layer, a back layer on the side of the support opposite the silver halide emulsion layer and other auxiliary layers.

The compound of formula (I) may be incorporated in a single layer or in a plurality of layers as necessary. A plurality of compounds of the present invention may be incorporated in a single layer or in a plurality of layers separately or in admixture as necessary.

The compound of the present invention may be used in combination with various water-soluble dyes as mentioned above, water-soluble dyes adsorbed to mordant, emulsion-dispersed dyes or disperse solid dyes as necessary.

The hydrophilic colloid preferably used is gelatin. Various known gelatin may also be used. Examples of such known gelatin include gelatin produced by different methods, such as lime-treated gelatin, acid-treated gelatin, and gelatin obtained by chemical modification, e.g., phthalation and sulfonylation, of these gelatin. If necessary, these gelatin may be desalted before use.

The mixing ratio of the compound of formula (I) of the present invention and gelatin depends on the structure and added amount of the compound and is preferably in the range of $1/10^3$ to $\frac{1}{2}$.

The layer containing the compound of formula (I) of the present invention undergoes decomposition and elution with hydroquinone, sulfite or alkali contained in the developer upon development and, thus, does not stain or contaminate the photographic images developed. The time required for decoloration greatly depends on the concentration of hydroquinone in the developer or other processing baths, the amount of alkali or other nucleophilic reagent, the type, amount and added position of the compound of the present invention, the amount and degree of swelling of hydrophilic colloid, degree of agitation, etc. The time required for decoloration can be arbitrarily controlled according to the general rules of physical chemistry.

The pH value of the processing solution depends on the kind of processing, i.e., development, bleach or fixing and is normally in the range of 3.0 to 13.0, preferably 5.0 to 12.5. Thus, the compound of the present invention is characterized in that it can release a dye unit during processing having a relatively low pH value.

The silver halide emulsion to be used in the present invention preferably comprises silver bromide, silver bromoiodide, silver bromochloroiodide, silver bromochloride or silver chloride.

The silver halide grain to be used in the present invention may have a regular crystal form such as cubic and octahderon or irregular crystal form such as sphere and tablet or composite thereof. Alternatively, a mixture of grains having various crystal forms can be used. Regular crystal forms are preferred.

The silver halide grain to be used in the present invention may have different phases from core to surface or a uniform phase from core to surface. Further, the silver halide grain to be used in the present invention may be of the type in which latent images are mainly formed on the surface thereof (e.g., negative type emulsion) or of the type in which latent images are mainly formed thereinside (e.g., internal latent image type emulsion, previously fogged direct reversal type emulsion). Preferably, the negative type emulsion is used.

The silver halide emulsion to be used in the present invention is preferably an emulsion wherein tabular grains with a thickness of 0.5 μm or less, preferably 0.3 μm or less, a diameter of preferably 0.6 μm or more and an average aspect ratio of 5 or more account for 50% or more of all the grains as calculated in terms of projected area or a monodisperse emulsion wherein the statistic fluctuation coefficient (value S/d⁻ obtained by dividing the standard deviation S by the diameter d⁻ in a the distribution of diameter of projected area approximated to circle) is 20% or less. Two or more of the tabular grain emulsions and monodisperse emulsions may be used in admixture.

The preparation of the photographic emulsion to be used in the present invention can be accomplished by any suitable methods as described in P. Glafkides, *Chimie Physique Photographeque*, Paul Montel, 1967, G. F. Duffin, *Photographic Emulsion Chemistry*, Focal Press, 1966, and V. L. Zelikman et al., *Making and Coating Photographic Emulsion*, Focal Press, 1964.

In order to control the growth of grains during the formation of silver halide grains, silver halide solvents there can be used including ammonia, potassium thiocyanate, ammonium thiocyanate, thioether compounds as described in U.S. Pat. Nos. 3,271,157, 3,574,628, 3,704,130, 4,297,439, 4,276,374, thione compounds as described in JP-A-53- 144319, 53-82408 and 55-77737, and amine compounds as described in JP-A-54-100717.

In the process of formation or physical ripening of silver halide grains, cadmium salts, zinc salts, thallium salts, iridium salts or complexes thereof, rhodium salts or complexes thereof, or iron salts or complexes thereof may be present in the system.

In order to contrast-develop a silver halide photographic material for photomechanical process as preferred embodiment of the present invention, a hydrazine derivative or tetrazolium compound can be used.

As a binder or protective colloid to be incorporated in the emulsion layer or interlayer in the light-sensitive material of the present invention, gelatin may be advantageously used. Other hydrophilic colloids may also be used. Examples of such hydrophilic colloids which can be used in the present invention include protein such as gelatin derivatives, graft polymer of gelatin with other high molecular compounds, albumin, and casein, saccharide deativatives such as hydroxyethyl cellulose, carboxymethyl cellulose, cellulose ester sulfate, sodium alginate, and starch derivatives, monopolymers or copolymers such as polyvinyl alcohol, polyvinyl alcohol partial acetal, poly-N-vinyl pyrrolidone, polyacrylic acid, polymethacrylic acid, polyacrylamide, polyvinyl imidazole, and polyvinyl pyrazole, and other various synthetic hydrophilic high molecular compounds.

Examples of gelatin which can be used include lime-treated gelatin, acid-treated gelatin, or enzyme-treated gelatin as described in *Bull. Soc. Sci. Phot.*, Japan, No. 16, 1966, page 30. Hydrolyzate of gelatin may also be used.

The photographic emulsion and light-insensitive hydrophilic colloid may comprise an inorganic or organic film hardener in any hydrophilic colloidal layer constituting the photographic light-sensitive layer or back layer. Specific examples of such a film hardener include chromium salts, aldehydes (e.g., formaldehyde, glyoxal, glutaraldehyde), and N-methylol compounds (e.g., dimethylolurea). Active halogen compounds (e.g., 2,4-dichloro-6-hydroxy-1,3,5-triazine and sodium salts thereof) and active vinyl compounds (e.g., 1,3-bisvinylsulfonyl-2-propanol, 1,2-bis(vinylsulfonylacetamide)ethane, bis(vinylsulfonylmethyl) ether or vinyl polymer containing vinylsulfonyl group in side chains) are preferred because they can cure hydrophilic colloid such as gelatin fast to give stable photographic properties. N-carbamoylpyridinium salts (e.g., (1-morpholinocarbonyl-3-pyridinio)methanesulfonate) and haloamidinium salts (e.g., 1-(1-chloro-1-pyridinomethylene)pyrolidinium-2-naphthalene sulfonate) are also excellent because of their fast curing speed.

The photographic emulsion used in the present invention may be subjected to spectral sensitization with a methine dye or the like. Examples of such a dye include cyanine dye, melocyanine dye, composite cyanine dye, composite melocyanine dye, holopolar cyanine dye, hemicyanine dye, styryl dye and hemioxonol dye. Particularly preferred among these dyes are cyanine dye, melocyanine dye and composite melocyanine dye. Any of nucleus which are commonly used as basic heterocyclic nucleus for cyanine dye can be applied to these dyes. Examples of suitable nucleus which can be applied to these dyes include a pyrroline nucleus, a oxazoline nucleus, a thiazoline nucleus, a pyrrole nucleus, a oxazole nucleus, a thiazole nucleus, a selenazole nucleus, an imidazole nucleus, a tetrazole nucleus, a pyridine nucleus and a nucleus obtained by fusion of alicyclic hydrocarbon rings to the afore mentioned nuclei or a nucleus obtained by fusion of aromatic hydrocarbon rings to nucleus groups, e.g., indolenine nucleus, benzindolenine nucleus, indole nucleus, benzoxazole nucleus, naphthooxazole nucleus, benzothiazole nucleus, naphthothiazole nucleus, benzoselenazole nucleus, benzimidazole nucleus and quinoline nucleus. These nuclei may contain a substituent on its carbon atoms.

Examples of suitable nucleus which can be applied to melocyanine dye or composite melocyanine dye include those having a ketomethylene structure such as a 5- or 6-membered heterocyclic nucleus, e.g., pyrazoline-5-one nucleus, thiohydantoin nucleus, 2-thiooxazoline-2,4-dione nucleus, thiazoline-2,4-dione nucleus, rhodanine nucleus, and thiobarbituric acid nucleus.

These sensitizing dyes can be used singly or in combination. Such a combination of sensitizing dyes is often used particularly for the purpose of supersensitization. A dye which does not exhibit a spectral sensitizing effect or a substance which does not substantially absorb visible light but exhibits a supersensitizing effect may be incorporated in the emulsion together with such a sensizing dye. For example, an aminostilbene compound substituted by nitrogen-containing heterocyclic group as described in U.S. Pat. Nos. 2,933,390 and 3,635,721, an aromatic organic acid-formaldehyde condensates as described in U.S. Pat. No. 3,743,510, cadmium salts, an azaindene compounds or the like may be incorporated in the emulsion. Combinations as described in U.S. Pat. Nos. 3,615,613, 3,615,641, 3,617,295, and 3,635,721 are particularly useful.

The silver halide photographic emulsion to be used in the present invention may comprise various compounds for the purpose of inhibiting fogging during the preparation, storage or photographic processing of the light-sensitive material or stabilizing the photographic properties of the light-sensitive material. Examples of such compounds which may be incorporated in the photographic emulsion include many compounds known as fog inhibitors or stabilizers, such as azoles, e.g., benzothiazolium salt, nitroimidazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles, mercaptotetrazoles (particularly 1-phenyl-5-mercaptotetrazole), mercaptopyrimidines, mercaptotriazines, thioketo compounds, e.g., oxazolinethione, azaindenes, e.g., triazaindenes, tetrazaindenes (particularly 4-hydroxy-substituted (1,3,3a,7)tetraazaindenes), pentaazaindenes, benzenesulfonic acid, benzenesulfinic acid, and amide benzenesulfonate.

The light-sensitive material of the present invention may comprise one or more surface active agents for the purpose of facilitating coating and emulsion dispersion, inhibiting electric charging and adhesion, improving smoothness and photographic properties (e.g., acceleration of development, higher contrast, sensitization) or similar purposes.

The light-sensitive material prepared according to the present invention may contain a water-soluble dye in a hydrophilic colloidal layer as a filter dye or for the purpose of inhibiting irradiation or halation or other purposes. Preferred examples of such a dye include oxonol dye, hemioxonol dye, styryl dye, melocyanine dye, anthraquinone dye, and azo dye. Other useful examples of such a dye include cyanine dye, azomethine dye, triarylmethane dye, and phthalocyanine dye. An oil-soluble dye may be emulsified by an oil-in-water dispersion method and then incorporated in a hydrophilic colloidal layer.

The present invention can be applied to a multi-layer multi-color photographic light-sensitive material having at least two different spectral sensitivities on a support. The multi-layer multi-color photographic light-sensitive material normally comprises at least one red-sensitive emulsion layer, at least one green-sensitive emulsion layer and at least one blue-sensitive layer on a support. The order of arrangement of these layers can be properly selected as necessary. In a preferred embodiment, the order of arrangement of layers is red-sensitive emulsion layer, green-sensitive emulsion layer and blue-sensitive emulsion layer, blue-sensitive emulsion layer, green-sensitive emulsion layer and red-sensitive emulsion layer or blue-sensitive emulsion layer, red-sensitive emulsion layer and green-sensitive emulsion layer as viewed from the support side. An emulsion layer having the same color sensitivity may be composed of two or more emulsion layers having different sensitivities to improve the resulting sensitivity. A three-layer structure may be employed to improve graininess. A light-insensitive layer may be provided between two or more emulsion layers having the same color sensitivity. A emulsion layer having another color sensitivity may be inserted between emulsion layers having the same color sensitivity. A reflective layer comprising finely divided silver halide grains may be provided under a high sensitivity layer, particularly high sensitivity blue-sensitive layer to improve sensitivity.

In general, the red-sensitive emulsion layer contains a cyan-forming coupler, the green-sensitive emulsion layer contains a magenta-forming coupler, and the blue-sensitive emulsion layer contains a yellow-forming coupler. Different combinations may be employed as necessary. For example, infrared-sensitive emulsion layers may be combined to provide a photographic light-sensitive material for false color photography or exposure by semiconductor laser.

In the photographic light-sensitive material of the present invention, the photographic emulsion layer and other layers are coated on a flexible support commonly used for photographic light-sensitive material such as plastic film, paper and cloth or a rigid support glass, earthenware and metal. Useful examples of such a flexible support include film made of a semisynthetic or synthetic high molecular compound such as cellulose nitrate, cellulose acetate, cellulose acetate butyrate, polystyrene, polyvinyl chloride, polyethylene terephthalate, and polycarbonate, and paper on which a baryta layer or α-olefin polymer (e.g., polyethylene, polypropyrene, ethylene-butene copolymer) is coated or laminated. The support may be colored with a dye or pigment. The support may be blackened for the purpose of screening light.

In the case of a silver halide photographic material for a photomechanical process as one of preferred embodiments of the present invention, the support preferably used is polyethylene terephthalate. The thickness of the support is not specifically limited and is preferably in the range of about 12 $\mu$m to 500 $\mu$m, more preferably about 40 $\mu$m to 200 $\mu$m in view of handleability and flexibility. In particular, biaxially oriented materials can be advantageously used in view of stability and strength.

More preferably, a support material comprising a water barrier layer made of a vinylidene chloride copolymer on both sides thereof can be used.

The thickness of the vinylidene chloride copolymer layer is preferably large to inhibit the expansion of the base due to water absorption upon development. However, if the vinylidene chloride copolymer is too thick, its adhesion to the silver halide emulsion layer becomes troublesome. Therefore, the thickness of the vinylidene chloride.copolymer layer is normally in the range of 0.3 to 5 $\mu$m, preferably 0.5 to 2.0 $\mu$m.

The coating of the photographic emulsion layer and other hydrophilic colloidal layers can be accomplished by any coating method such as dip coating method, roller coating method, curtain coating method and extrusion coating method. A number of layers may be simultaneously coated on a support by a coating method as described in U.S. Pat. Nos. 2,681,294, 2,761,791, 3,526,528, and 3,508,947 as necessary.

The present invention can be applied to various color and black-and-white light-sensitive materials. Typical examples of such light-sensitive materials include color negative films for general purposes and motion pictures, color reversal films for slides and television, color papers, color positive films, color reversal papers, color diffusion transfer type light-sensitive materials, and heat-developable color light-sensitive materials. The present invention can also be applied to a direct positive color light-sensitive material comprising an internal latent image type silver halide emulsion which has not been previously fogged as described in JP-A-63-159847. By utilizing a mixture of three color couplers as described in Research Disclosure, No. 17123, (July, 1978) or utilizing a black color-forming coupler as described in U.S. Pat. No. 4,126,461 and British Patent 2,102,136, the present invention can be applied to black-and-white light-sensitive materials for X-ray and the like. The present invention can be also applied to plate-making films such as lithographic film and scanner film, X-ray film for direct or indirect medical use or industrial use, negative black-and-white films for picture taking, blackand-white photographic papers, COM or ordinary microfilms, and print out type light-sensitive materials.

The light-sensitive material of the present invention may utilize various exposure means. Any light source which emitts radiation having a wavelength corresponding to the sensitive wavelength of the light-sensitive material can be used as an illuminating or writing light source. In general, natural light (sunshine), an incandescent lamp, a halogen atom-containing lamp, a mercury vapor lamp, a fluorescent tube, and a flash light such as stroboscope and metal combustion flash bulb can be used.

Alternatively, light sources which emit light having a wavelength ranging from ultraviolet region to infrared region, such as a gas, dye solution or semiconductor laser, a light-emitting diode and a plasma light source can be used as a recording light source.

Furthermore, a fluorescent screen (CRT) which emits light from a fluorescent substance excited by electronic rays, a liquid crystal display (LCD) or an exposure means obtained by combining a microshutter array utilizing lanthanum-doped titanium lead zirconiumate (PLZT) with a linear or planar light source can be used. If necessary, the spectral distribution used for exposure can be adjusted by a color filter.

The photographic processing of the light-sensitive material of the present invention can be effected by any suitable method and with any suitable processing solution as described in Research Disclosure, No. 17643, pp. 28-30. The photographic processing may be either black-and-white processing for forming silver images or color photographic processing for forming dye images. The processing temperature can be normally selected in the range of 18° C. to 50° C.

The developer to be used for black-and-white processing can comprise known developing agents. Examples of these developing agents include dihydroxybenzenes (e.g., hydroquinone), 3-pyrazolidones (e.g., 1-phenyl-3-pyrazolidone), and aminophenols (e.g., N-methyl-p-aminophenol), which can be used singly or in combination. The developer normally may further comprise known preservatives, alkaline agents, pH buffers or fog inhibitors. The developer may further comprise dissolution aids, color toners, development accelerators (e.g., quaternary salt, hydrazine, benzyl alcohol), surface active agents, anti-foaming agents, water hardeners, film hardeners (e.g., glutaraldehyde), thickening agents, etc.

In order to effect black-and-white reversal photographic processing of the light-sensitive material of the present invention, any known development processes for the formation of positive type silver images by reversal phenomenon can be used. Any known processing solutions can be used. The processing temperature can be selected in the range of 18° C. to 65° C. However, the processing temperature may fall below 18° C. or exceed 65° C.

The reversal development process normally consists of the following steps:

1st development—rinse—bleach—washing—total exposure—2nd development—fixing—rinse—drying The developer to be used for black-and-white processing at the 1st development can comprise known developing agents. Examples of these developing agents include dihydroxybenzenes (e.g., hydroquinone), 3-pyrazolidones (e.g., 1-phenyl-3-pyrazolidone), aminophenols (e.g., N-methyl-p-aminophenol), 1-phenyl-3-pyrazolidones, ascorbic acid, and heterocyclic compounds formed by condensation of 1,2,3,4-tetrahydroquinoline ring and indolenine ring as described in U.S. Pat. No. 4,067,872, singly or in combination. In particular, dihydroxybenzenes may be preferably used in combination with pyrazolidones and/or aminophenols. The developer normally may further comprise known preservatives, alkaline agents, pH buffers or fog inhibitors. The developer may further comprise dissolution aids, color toners, development accelerators, surface active agents, anti-foaming agents, water hardeners, film hardeners, thickening agents, etc. The light-sensitive material of the present invention may be normally processed with a processing solution containing sulfurous ions as preservative in an amount of 0.15 mol/l or more.

The pH value of the developer is normally in the range of 8.5 to 11, particularly 9.5 to 10.5.

The 1st developer comprises a silver halide solvent such as NaSCN in an amount of 0.5 to 6 g/l.

Examples of the 2nd developer include a general purpose black-and-white developer, i.e., a composition obtained by removing the silver halide solvent from the 1st developer. The pH value of the 2nd developer is preferably in the range of 9 to 11, particularly 9.5 to 10.5.

The bleaching solution may comprise a bleaching agent such as potassium bichromate and cerium sulfate.

The fixing solution may preferably comprise thiosulfate or thiocyanate, and, optionally a water-soluble aluminum salt.

In a special form of development process, a light-sensitive material containing a developer in, for example, an emulsion layer, may be processed in an alkaline aqueous solution. If the developer is hydrophobic, it may be incorporated in the emulsion by any suitable method as described in Research Disclosure, No. 16928, U.S. Pat. No. 2,739,890, British Patent 813,253, and West German Patent 1,547,763.

Examples of the fixing solution incued any commonly used compositions. Examples of fixing agents include thiosulfate, thiocyanate, and organic sulfur compounds which are known to serve as fixing agents. The fixing solution may comprise a water-soluble aluminum salt as film hardener.

The color developer used for the development of the light-sensitive material of the present invention is preferably an alkaline aqueous solution containing as a main component an aromatic primary amine color developing agent. Examples of this color developing agent include an aminophenolic compound, preferably p-phenylenediamine compound. Typical examples of such a compound include 3-methyl-4-amino-N,N-diethylaniline, 3-methyl-4-amino-N-ethyl-N-β-hydroxyethylaniline, 3-methyl-4-amino-N-ethyl-β-methanesulfonamidethylaniline, 3-methyl-4-amino-ethyl-N-β-methoxyethylaniline, and sulfate, hydrochloride and p-toluenesulfonate thereof. These diamines are normally more stable and, thus, can be preferably used in the form of salt rather than in a free state.

The color developer to be used in the present invention normally contains a pH buffer such as carbonate, borate and phosphate of alkaline metal or development or fog inhibitor such as bromide, iodide, benzimidazole, benzothiazole and mercapto compound. As is necessary, the color developer may also contain a preservative such as hydroxylamine, dialkylhydroxylamine, hydrazine, triethanolamine, triethylenediamine and sulfite, an organic solvent such as triethanolamine and diethylene glycol, a development accelerator such as benzyl alcohol, polyethylene glycol, quaternary ammonium salt, and amine, a dye-forming coupler, a competing coupler, a nucleating agent such as sodium boron hydride, an auxiliary developing agent such as 1-phenyl-3-pyrazolidone, a viscosity builder, various chelating agents such as aminopolycarboxylic acid, aminopolyphosphonic acid, alkylphosphonic acid and phosphonocarboxylic acid, an oxidation inhibitor as described in West German Patent Application (OLS) 2,622,950, or the like.

In the development of a reversal color light-sensitive material, black-and-white development is normally effected before color development. The black-and-white developer may comprise known black-and-white developing agents such as dihydroxybenzene (e.g., hydroquinone), 3-pyrazolidone (e.g., 1-phenyl-3-pyrazolidone) and aminophenol (e.g., N-methyl-p-amionophenol), which may be used singly or in combination.

Any color developer as well as any photographic developing method can be applied to the light-sensitive material of the present invention. Examples of developing agent to be incorporated in the developer include dihydroxybenzene developing agent, 1-phenyl-3-pyrazolidone developing agent, and p-aminiphenolic developing agent. These developing agents can be used singly or in combination (e.g., a combination of 1-phenyl-3-pyrazolidone and dihydroxybenzene and a combination of p-aminophenol and dihydroxybenzene). Alternatively, the light-sensitive material of the present invention may be processed with an infectious developer comprising hydroquinone and a sulfurous ion buffer such as carbonyl bisulfite.

Examples of dihydroxybenzene developing agents include hydroquinone, chlorohydroquinone, bromohydroquinone, isopropylhyd roquinone, toluhydrohydroquinone, methylhydroquinone, 2,3-dichlorohydroquinone, and 2,5-dimethylhydroquinone. Examples of 1-phenyl-3-pyrazolidone developing agents include 1-phenyl-3-pyrazolidone, 4,4- dimethyl-1-phenyl-3-pyrazolidone, 4-hydroxymethyl-4'-methyl-1-phenyl-3-pyrazolidone, and 4,4-dihydroxymethyl-1-phenyl-3-pyrazolidone.

Examples of p-aminophenolic developing agents include p-aminophenol, and N-methyl-p-aminophenol.

The developer used in the present invention may comprise a compound which gives rise to free sulfurous ions as a preservative, such as sodium sulfite, potassium sulfite, potassium metabisulfite and sodium bisulfite. The infectious developer may comprise sodium formaldehyde busulfite, which gives little or no free sulfurous ions therein.

Examples of the alkaline agent incorporated in the developer include potassium hydroxide, sodium hydroxide, potassium carbonate, sodium carbonate, sodium acetate, tribasic potassium phosphate, diethanolamine, and triethanolamine. The pH value of the developer is normally adjusted to 8.5 or more, preferably 9.5 or more.

The developer may comprise an organic compound known as a fog inhibitor or a development inhibitor. Examples of such an organic compound include azoles such as benzothiazolium, nitroindazole, nitrobenzimidazole, chlorobenzimidazole, bromobenzimidazole, mercaptothiazole, mercaptobenzothiazole, mercaptobenzimidazole, mercaptothiadiazole, aminotriazole, benzotriazole, nitrobenzotriazole, and mercaptotetrazole (particularly 1-phenyl-5-mercaptotetrazole ), mercaptopyrimidine, mercaptotriazine, thioketo compound such as oxazolinethione, azaindene such as triazaindene, tetraazaindene (particularly 4-hydroxy-substituted (1,3,3a,7)tetraazaindene), and pentaazaindene, benzenethiosulfonic acid, benzenesulfinic acid, amide benzenesulfonate, and sodium 2-mercaptobenzimidazole-5-sulfonate.

The developer used in the present invention may comprise, as a development inhibitor, a polyalkylene oxide as described above, for example, a polyethylene oxide having a molecular weight of 1,000 to 10,000 in an amount of 0.1 to 10 g/l.

The developer to be used in the present invention may comprise, as a water hardener, nitrilotriacetic acid, ethylenediaminetetraacetic acid, triethylenetetraamine, acetic acid, diethylenetetraaminepetaacetic acid, or the like.

The developer used in the present invention may comprise a compound as described in JP-A-56-24347 as a silver stain inhibitor, a compound as described in JP-A-62-212651 as a development unevenness inhibitor, and a compound as described in JP-A-61-267759 as a dissolution aid.

The developer used in the present invention may comprise, as a buffer, boric acid as described in JP-A-62-186259 and saccharides (e.g., saccharose), oximes (e.g., acetoxime), phenols (e.g., 5-sulfosalicylic acid), and tribasic phosphate (e.g., sodium salt, potassium salt) as described in JP-A-60-93433.

Examples of the development accelerator used in the present invention include any type of compound. These compounds may be incorporated in the light-sensitive material or any of the processing solutions. Preferred examples of development accelerators include an amine compound, an imidazole compound, an imidazoline compound, a phosphonium compound, a sulfonium compound, a hydrazide compound, a thioether compound, a thione compound, certain kinds of mercapto compounds, a mesoionic compound, and a thiocyanate.

These development accelerators are particularly required to effect rapid development in a short time and are preferably incorporated in the color developer. However, these development accelerators are preferably incorporated in the light- sensitive material depending on the kind of hight-sensitive material used or the position of the light-sensitive layer to be development-accelerated on the support. These development accelerators may be incorporated both in the color developer and in the light-sensitive material. If necessary, a color developing bath may be provided with a prebath in which these development accelerators are incorporated.

Useful examples of amino compounds include inorganic amine such as hydroxylamine and organic amine. Examples of an organic amine include an aliphatic amine, an aromatic amine, a cyclic amine, an aliphatic-aromatic mixed amine, and a heterocyclic amine. Primary, secondary and tertiary amines and quaternary ammonium compounds also are effective.

The photographic emulsion layer which has been subjected to color development is normally then subjected to bleach. The bleach may be effected simultaneously with or separately from fixing. In order to further expedite the processing, the bleach may be followed by blix. Examples of the bleaching agent include a compound of polyvalent metal such as iron (III), cobalt (III), chromium (IV) and copper (II), peracid, quinone, nitroso compound or the like. Typical examples of such a bleaching agent include ferricyanides, bichromates, complex salts of iron (III) or cobalt (III) with an organic acid such as aminopolypolycarboxylic acid (e.g., ethylenediaminetetraacetic acid, diethylenetriaminepentaacetic acid, nitrilotriacetic acid, and 1,3-diamino-2-propanoltetraacetic acid), citric acid, tartaric acid and malic acid, persulfates, manganates, and nitrosophenol. Among these bleaching agents, ferric ethylenediaminetetraacetate, ferric diethylenetriaminepentaacetate and persulfate may be preferably used in view of rapidity of processing and environmental protection. Furthermore, ferric ethylenediaminetetraacetate complex is particularly useful for a single bleaching bath and a combined bleach and fixing bath.

The bleaching solution, blix solution and their pre-baths may comprise a bleach accelerator as necessary. Specific examples of useful bleach accelerators include compounds containing a mercapto group or a disulfide group as described in U.S. Pat. No. 3,893,858, West German Patents 1,290,812 and 2,059,988, JP-A-53-32736, 53-57831, 53-37418, 53-65732, 53-72623, 53-95630, 53-95631, 53-104232, 53-124424, 53-141623, and 53-28426, and Research Disclosure, No. 17129 (July, 1978), thiazolidine derivatives as described in JP-A-50-140129, thiourea derivatives as described in JP-B-45-8506 (the term "JP-B" as used herein means an "examined Japanese patent publication"), JP-A-52-20832, and 53-32735, and U.S. Pat. No. 3,706,561, iodides as described in West German Patent 1,127,715, and JP-A-58-16235, polyethylene oxides as described in West German Patent 966,410, and 2,748,430, polyamine compounds as described in JP-B-45-8836, compounds as described in JP-A-49-42434, 49-59644, 53-94927, 54-35727, 55-26506, and 58-163940, iodine ions, and bromine ions. Among these bleach accelerators, compounds containing a mercapto group or a disulfide group may be preferably used in view of the accelerating effect. Particularly, compounds as described in U.S. Pat. No. 3,893,858, West German Patent 1,290,812, and JP-A-53-95630 are preferably used. Furthermore, compounds as described in U.S. Pat. No. 4,552,834 are preferably used.

These bleach accelerators may be incorporated in the light-sensitive material. When a color light-sensitive material for picture taking is subjected to blix, the afore mentioned bleach accelerators are particularly effective.

Examples of fixing agents to be used in the present invention include thiosulfate, thiocyanate, thioether compound, thiourea, and iodide (which is used in a large amount). Thiosulfates are normally used. Examples of a preservative for a blix solution or a fixing solution include sulfite, bisulfite or a carbonyl-bisulfurous acid adduct.

The blix or fixing step is normally followed by rinse and stabilizing steps. For the purpose of inhibiting precipitation and saving water, various known compounds may be incorporated in the rinsing bath and stabilizing bath. For example, in order to inhibit precipitation, a water hardener such as inorganic phosphoric acid, aminopolycarboxylic acid, organic aminopolyphosphonic acid and organic phosphoric acid, a germicide or anti-fungal agent for the inhibition of proliferation of various bacteria or algae, a metallic salt such as magnesium salt, aluminum salt and bismuth salt, a surface active agent for the inhibition of drying load or unevenness, and various film hardeners may be used as necessary. Alternatively, compounds as described in L. E. West, "Photographic Science and Engineering", vol. 6, pp. 344–359 (1965) can be used. In particular, chelating agents or anti-fungal agents may be preferably used.

The rinsing step is normally effected in two or more baths wherein the rinsing water flows backward to save water. Instead of the rinsing step, a multi-stage countercurrent stabilizing step as described in JP-A-57-8543 can be effected. In this case, 2 to 9 baths wherein the processing solution flows backward are needed. Besides the above-mentioned additives, the stabilizing bath may comprise various compounds for the purpose of stabilizing images. Typical examples of these compounds include various buffers for adjusting the pH value of film, for example, to 3 to 9, (e.g., borate, metaborate, borax, phosphate, carbonate, potassium hydroxide, sodium hydroxide, aqueous ammonia, monocarboxylic acid, dicarboxylic acid, polycarboxylic acid, in combination), and aldehyde such as formalin.

Furthermore, other various additives such as chelating agents (e.g., inorganic phosphoric acid, aminopolycarboxylic acid, organic phosphoric acid, aminopolysulfonic acid, phosphonocarboxylic acid), germicide (benzoisothiazolinone, isothiazolone, 4-thiazolinebenzimidazole, halogenated phenol, sulfanylamide, benzotriazole), surface active agents, fluorescent brightening agents, and film hardeners may be used. Two or more compounds for the same or different purposes may be used in combination.

Example of pH adjustors for processed films preferably include various ammonium salts such as ammonium chloride, ammonium nitrate, ammonium sulfate, ammonium phosphate, ammonium sulfite, and ammonium thiosulfate.

In the case of color light-sensitive materials for picture taking, the rinse-stabilization step which is normally effected after fixing may be replaced by the above mentioned stabilizing step and rinsing step (which is water saving). In this case, if the magenta coupler is two- equivalent, the stabilizing bath may be free of formalin.

The rinsing and stabilizing time depends on the type of the light-sensitive material and the processing conditions and is normally in the range of 20 seconds to 10 minutes, preferably 20 seconds to 5 minutes.

The silver halide color light-sensitive material of the present invention may comprise a color developing agent for the purpose of simplifying and expediting processing. Such a color developing agent may be preferably incorporated in the form of precursor.

Examples of such a precursor include indoaniline compounds as described in U.S. Pat. No. 3,342,597, Schiff base type compounds as described in U.S. Pat. No. 3,342,599, and Research Disclosure, Nos. 14850 and 15159, aldol compounds as described in Research Disclosure, No. 13924, metal complexes as described in U.S. Pat. No. 3,719,492, urethane compounds as described in JP-A-53-135628, and various salt type precursors as described in JP-A-56-6235, 56-16133, 56-59232, 56-67842, 56-83734, 56-83735, 56-83736, 56-89735, 56-81837, 56-54430, 56-106241, 56-107236, 57-97531, and 57-83565.

The silver halide color light-sensitive material of the present invention may comprise various 1-phenyl-3-pyrazolidones for the purpose of accelerating color development as necessary. Typical examples of such compounds are described in JP-A-56-64339, 57-144547, 57- 211147, 58-50532, 58-50536, 58-50533, 58-50534, 58-50535, and 58-115438.

In the present invention, the various processing solutions are used at a temperature of 10° C. to 50° C. While the processing solution temperature is normally in the range of 33° C. to 38° C, a high temperature may be used to accelerate the processing and thus reduce the processing time or a lower temperature may be used to improve the picture quality or the stability of the processing solutions. In order to save silver to be incorporated in the light-sensitive material, the processing using cobalt intensification or hydrogen peroxide intensification as described in West German Patent 2,226,770 and U.S. Pat. No. 3,674,499 may be effected.

A heater, temperature sensor, level sensor, circulating pump, filter, floating cover, squeegee or the like may be provided in the various processing baths.

In continuous processing, the various procesing solutions may be replenished to inhibit the fluctuation in the composition of the solution, providing a constant finish. The replenishment rate may be reduced to half or less of the standard value to reduce cost.

If the light-sensitive material of the present invention is a color paper, it may be processed normally. If the light-sensitive material of the present invention is a color photographic material for picture-taking, it may be subjected to blix as necessary.

In the present invention, the development time means the time between the point at which the leading end of the photographic light-sensitive material enters into the developer and the point at which it comes out from the final drying zone.

The present invention will be further described in the following examples, but the present invention should not be construed as being limited thereto.

EXAMPLE 1

On a 180-μm thick polyethylene terephthalate support having a gelatin subbing layer on one side thereof were coated the following compositions:

(1) a layer containing gelatin in an amount of 2.0 g/m$^2$ and 1,3-vinylsulfonyl-2-propanol; and (2) a layer containing gelatin in an amount of 1.0 g/m$^2$, a compound as set forth in Table 1 in an amount of 0.12 mmol/m$^2$, the following betainic surface active agent:

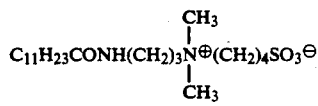

in an amount of 0.17 mmol/m$^2$ and 1,3-divinylsulfonyl-2-propanol.

The compound as set forth in Table 1 was added to the system with stirring in the form of solution in a small amount of dimethylformamide before the addition of the film hardener to the coating solution for the layer (2).

These coat specimens (1-3 to 1-7) were then measured for spectral absorption characteristics by means of Type U-3210 spectrophotometer available from Hitachi Limited. The maximum absorption wavelength, absorbance at the maximum absorption wavelength and half band width are set forth in Table 1.

A comparative specimen (1-1) was prepared by coating on the support a layer comprising gelatin in an amount of 1.0 g/m$^2$ and 1,3-divinylsulfonyl-2-propanol and having the following dye A' (0.12 mmol/m$^2$) dispersed therein by the method as described in an example in International Patent Application Disclosure (WO)88/04794 instead of the layer (2).

Dye A'

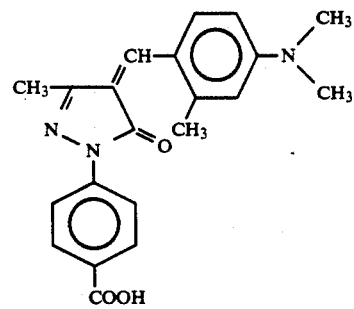

Another comparative specimen (1-2) was prepared by coating on the support a layer comprising gelatin in an amount of 1.0 g/m$^2$, the following dye B in an amount of 0.12 mmol/m$^2$ and 1,3-vinylsulfonyl-2-propanol instead of layer (2).

The dye B' was added to the system in the form of aqueous solution.

Dye B'

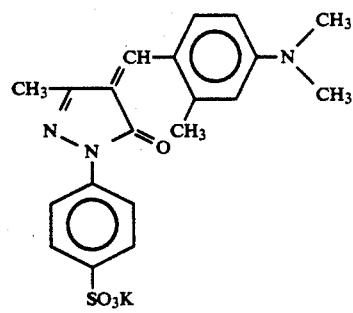

A comparative compound having the following formula wherein the elimination reactivity nucleus contains substituents with a small number of carbon atoms was prepared. A coating solution was prepared from the comparative compound in the same manner as in the compound of the present invention. However, the coating solution was gelated and thus could not be coated on the support.

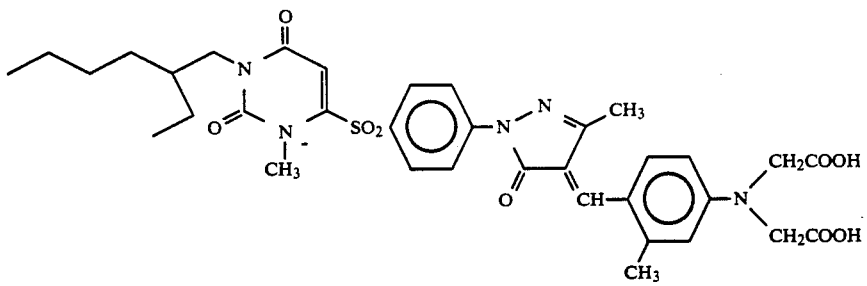

TABLE 1

| Coat Specimen No. | Compound No. | Maximum absorption wavelength (nm) | Absorbance | Half band width (nm) | Fixing rate (%) |
|---|---|---|---|---|---|
| 1-1 (Comparison) | A' | 505 | 0.166 | 208 | 99 |
| 1-2 (Comparison) | B' | 491 | 0.625 | 73 | 0 |
| 1-3 (Invention) | 1 | 409 | 0.260 | 121 | 95 |
| 1-4 (Invention) | 2 | 465 | 0.334 | 87 | 94 |
| 1-5 (Invention) | 3 | 517 | 0.775 | 96 | 93 |
| 1-6 (Invention) | 10 | 432 | 0.385 | 79 | 94 |
| 1-7 (Invention) | 15 | 480 | 0.323 | 93 | 93 |

Table 1 shows that as compared to the disperse solid dye A', the compounds of the present invention generally exhibit a small half band width and, thus, a sharp absorption characteristic and show a large absorbance. Obviously, this means that the dyes of the present invention exhibit excellent properties as a filter dye and also exhibit excellent properties as an antihalation dye for light-sensitive material sensitive to a characteristic wavelength.

EXAMPLE 2

The specimen as prepared in Example 1 was dipped in a phosphoric acid buffer with a pH value of 5 for 5 minutes, lightly washed with water, and then dried. The fixing rate (%) was then determined by dividing the absorbance obtained after dipping by the absorbance obtained before dipping. The results are set forth in Table 1.

Table 1 shows that as compared to the water-soluble dye B', the dyes of the present invention are substantially sufficiently fixed. This means that the dyes of the present invention can be fixed in a specific layer.

Overall the compounds of the present invention achieve superior results with respect to half band with, absorbance and fixing rate (%).

EXAMPLE 3

Comparative Specimen No. 1-8 was prepared in the same manner as in Example 1 except that the dye incorporated in layer (2) was replaced by the following dye included in preferred examples in JP-A-63-280246:

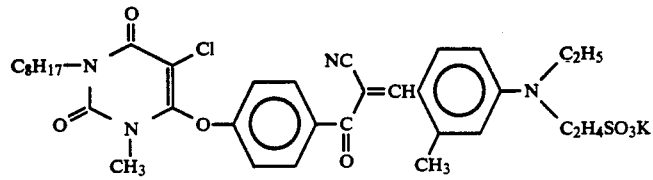

Comparative Specimen Nos. 1-3 and 1-7 were developed at a temperature of 38° C. for 20 seconds by means of an automatic processor FG-310PTS available from Fuji Photo Film Co., Ltd. to effect a decoloration test. These processed and dried specimens were then subjected to an aging test at a temperature of 50° C. and a relative humidity of 65% for 3 days. These specimens were then measured for absorbance to determine the percent color remaining with respect to the absorbance obtained before processing. The developer used was LD-835 available from Fuji Photo Film Co., Ltd. The fixing solution used was LF-308 available from Fuji Photo Film Co., Ltd.

The results are set forth in Table 2.

TABLE 2

| Coat Specimen No. | Residual color (%) | |
|---|---|---|
| | After processing | After 50° C.-65%-3 day ageing |
| 1-3 (invention) | Substantially zero | Substantially zero |
| 1-7 (invention) | " | " |
| 1-8 (comparison) | 17 | 27 |

Table 2 shows that the compound of the present invention exhibits excellent decolorability, causing little residual color.

EXAMPLE 4

Emulsion X was prepared as follows:

A 2.9M aqueous solution of silver nitrate and an aqueous solution of halogen salt containing 3.0M of sodium chloride and $5.3 \times 10^{-5}$M of ammonium hexachlororhodiumate (III) were added to a gelatin solution of sodium chloride with a pH value of 2.0 at a temperature of 38° C. with stirring at a constant potential of 100 mV for 4 minutes to form nuclei. After 1 minute, a 2.9M aqueous solution of silver nitrate and an aqueous solution of halogen salt containing 3.0M of sodium chloride were added to the system at a temperature of 38° C. at a constant potential of 100 mV at a speed half the value during the nucleus formation for 8 minutes. After the formation of grains, an ordinary flocculation method was used to effect rinsing. Gelatin was added to the system so that the pH and pAg values thereof were adjusted to 5.7 and 7.4, respectively. The stabilizer added to the system was 5,6-trimethylene-7-hydroxy-s-triazolo(2,3-a)pyrimidine in an amount of 0.05 mol per mol of silver. The resulting emulsion comprised cubic silver chloride grains with an average grain size of 0.13 μm containing rhodium in an amount of $8.0\times10^{-6}$ mol per mol of silver (fluctuation coefficient: 11%).

Emulsion Y was prepared as follows:

A 2.9M aqueous solution of silver nitrate and an aqueous solution of halogen salt containing 2.6M of sodium chloride, 0.4M of potassium bromide and $5.3\times10^{-5}$M of ammonium hexachlororhodiumate (III) were added to a gelatin solution of sodium chloride with a pH value of 2.0 at a temperature of 40° C. with stirring at a constant potential of 85 mV for 4 minutes to form nuclei. After 1 minute, a 2.9M aqueous solution of silver nitrate and an aqueous solution of halogen salt containing 2.6M of sodium chloride and 0.4M of potassium bromide were added to the system at a temperature of 40° C. at a constant potential of 85 mV at a speed half the value during the nucleus formation for 8 minutes. After the formation of grains, an ordinary flocculation method was used to effect rinsing. Gelatin was added to the system so that the pH and pAg values thereof were adjusted to 5.7 and 7.4, respectively. The stabilizer added to the system was 6-methyl-4-hydroxy-1,3,3a,7-tetraazaindene in an amount of $3.0\times10^{-3}$ mol per mol of silver. The resulting emulsion comprised cubic silver chloride grains with an average grain size of 0.16 μm containing rhodium in an amount of $8.0\times10^{-6}$ mol per mol of silver (Br content: 15%; fluctuation coefficient: 12%).

1-phenyl-5-mercaptotetrazole in an amount of 2.5 mg/m², an ethyl acrylate latex (average grain diameter: 0.05 μm) in an amount of 770 mg/m², and 2-bis(vinylsulfonylacetamide)ethane as film hardener in an amount of 126 mg/m² were added to Emulsion X and Emulsion Y. These emulsions were each coated on a polyester support in an amount of 3.6 g/m² as calculated in terms of silver (1.5 g/m² as calculated in terms of gelatin).

A lower protective layer containing 0.8 g/m² of gelatin, 8 mg/m² of lipoic acid, and 230 mg/m² of an ethyl acrylate latex (average grain diameter: 0.05 μm) were coated on the coated materials. An upper protective layer containing 3.2 g/m² of gelatin and comparative and present dyes as set forth in Table 3 were further coated on the coated materials. At the same time, a matting agent (silicon dioxide; average grain diameter: 3.5 μm) in an amount of 55 mg/m², methanol silica (average grain diameter: 0.02 μm) in an amount of 135 mg/m², sodium dodecylbenzenesulfonate as coating aid in an amount of 25 mg/m², sodium salt of sulfuric ester of polyoxyethylenenonylphenylether (polymerization degree: 5) in an amount of 20 mg/m², and potassium salt of N-perfluorooctanesulfonyl-N-propylglycine in an amount of 3 mg/m² were coated on the coated materials.

The base used in this example comprised the following back layer and back protective layer (percent swelling on the back side: 110%):

| (Back layer) | |
|---|---|
| Gelatin | 170 mg/m² |
| Sodium dodecylbenzenesulfonate | 32 mg/m² |
| Sodium dihexyl-α-sulfosuccinate | 35 mg/m² |
| SnO₂/Sb(9/1 by weight; average grain diameter: 0.25 μm) | 318 mg/m² |
| (Back protective layer) | |
| Gelatin | 2.7 mg/m² |
| Silicon dioxide matting agent (average grain diameter: 3.5μ) | 26 mg/m² |
| Sodium dihexyl-α-sulfosuccinate | 20 mg/m² |
| Sodium dodecylbenzenesulfonate | 67 mg/m² |

-continued

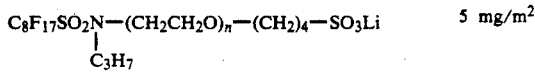

5 mg/m²

Dye A

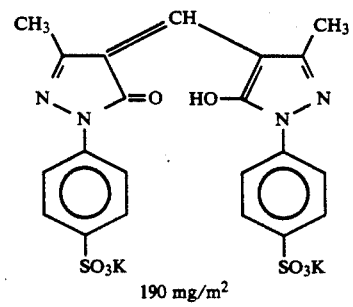

190 mg/m²

Dye B

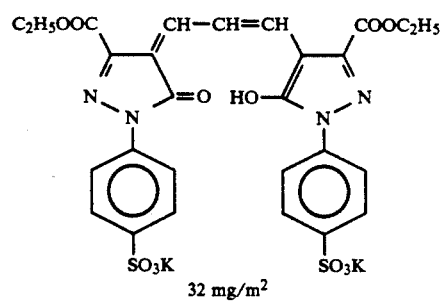

32 mg/m²

Dye C

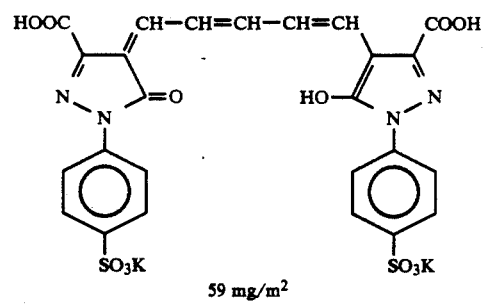

59 mg/m²

| Ethyl acrylate latex (average grain diameter: 0.05 μm) | 260 mg/m² |
|---|---|
| 1,3-Divinyl-sulfonyl-2-propanol | 149 mg/m² |

Photographic Properties

The specimens thus obtained were exposed to light through an optical wedge by means of a printer P-617DQ available from Dainippon Screen Mfg. Co., Ltd., developed with a developer LD-835 available from Fuji Photo Film Co., Ltd. at a temperature of 38° C. for 20 seconds, fixed, washed with water, and then dried (automatic processor FG-800RA). These specimens were then evaluated for the following properties:

1) Relative sensitivity: reciprocal of the exposure giving a density of 1.5, relative to that of Specimen 1 as 100;

2) γ: (3.0–0.3)/−{log(exposure giving a density of 0.3)−log(exposure giving a density of 3.0)}

These specimens were also evaluated for letter image quality. For this evaluation, these specimens were exposed to light in the form of lamination with originals and a laminated base as follows.

(a) Transparent or semitransparent laminated base;
(b) Line original (dark portion indicates line original);
(c) Transparent or semitransparent laminated base;
(d) Halftone original (dark portion indicates halftone);
(e) Light-sensitive material for dot to dot work Letter image quality 5 is a very good quality such that a letter with a width of 30 μm can be reproduced when exposure is effected in such a manner that a 50% halftone area on the original turns out 50% halftone area on the reflecting light-sensitive material. On the other hand, letter image quality 1 is a poor quality such that only a letter with a width of 150 μm or more can be reproduced under the same exposure conditions. Letter image qualities 2, 3 and 4 are organoleptically defined between letter image qualities 1 and 5. Letter image quality 3 or higher are practicable levels.

None of these processed specimens exhibit color remaining. The table shows that these specimens exhibit an excellent letter image quality without impairing sensitivity and gradation. Thus, desired properties can be secured at the dot to dot work stage.

TABLE 3

| Coat Specimen No. | Emulsion | Dye | Added amount of dye (mg/m²) | Relative sensitivity | γ | Letter image quality |
|---|---|---|---|---|---|---|
| 4-1 | X | Comparative Dye D | 10 | 100 | 7.5 | 1.5 |
| 4-2 | " | 1 | 50 | 99 | 7.9 | 3.5 |
| 4-3 | Y | Comparative Dye D | 15 | 100 | 5.5 | 1.5 |
| 4-4 | " | 1 | 70 | 99 | 5.8 | 3.5 |

The dye used for comparisor was comparative Dye D set forth as follows.

Comparative Dye D

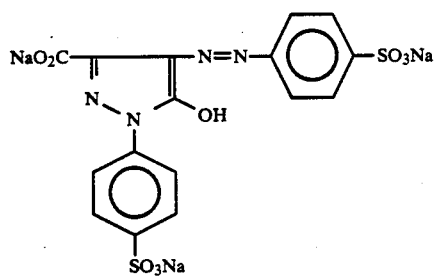

The comparative specimens were prepared according to Example 1 except comparative Dye D was used instead of compound 1.

EXAMPLE 5

Emulsion Z was prepared as follows:

A 2.9M aqueous solution of silver nitrate and an aqueous solution of halogen salt containing 3.0M of sodium chloride and $2.0 \times 10^{-5}$M of ammonium hexachlororhodiumate (III) were added to a gelatin solution of sodium chloride with a pH value of 2.0 at a temperature of 40° C. with stirring at a constant potential of 85 mV for 4 minutes to form nuclei. After 1 minute, a 2.9M aqueous solution of silver nitrate and an aqueous solution of halogen salt containing 3.0M of sodium chloride were added to the mixture at a temperature of 40° C. at a constant potential of 85 mV at a speed half the value during the nucleus formation for 8 minutes. After the formation of grains, an ordinary flocculation method was used to effect rinsing. Gelatin was added to the mixture so that the pH and pAg values thereof were adjusted to 5.7 and 7.4, respectively. The stabilizers added to the mixture was 5,6-trimethylene-7-hydroxy-s-triazolo(2,3- a)pyrimidine in an amount of $8 \times 10^{-3}$ mol per mol of silver and 6-methyl-4-hydroxy-1,3,3a,7-tetraazaindene in an amount of $1.5 \times 10^{-3}$ mol per mol of silver. The resulting emulsion comprised cubic silver chloride grains with an average grain size of 0.16 μm containing rhodium in an amount of $3.0 \times 10^{-6}$ mol per mol of silver (fluctuation coefficient: 12%).

The following hydrazine compound (Hz) in an amount of $4 \times 10^{-4}$ mol/mol Ag was added to Emulsion Z:

Hz

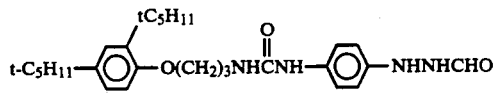

Then, a polyethyl acrylate latex in an amount of 30 wt. % based on gelatin as solid content and 1,3-vinylsulfonyl-2-propanol as film hardener was added. The emulsion was coated on a polyethylene terephthalate film in such an amount that the silver content reached 4.0 g/m². A yellow dye for improving safety to safelight as set forth in Table 4 was coated on the coat material. Specimen No. 5-1 was prepared as a comparison while Specimen No. 5-2 was prepared according to the present invention. The back layer was provided in the same manner as in Example 4.

Photographic Properties

The specimens thus prepared were exposed to light through an optical wedge original by means of a printer P-627FM, available from Dainippon Screen Mfg. Co., Ltd., developed with a developer GR-D1, available from Fuji Photo Film Co., Ltd., at a temperature of 38° C. for 20 seconds, fixed, washed with water, and then dried (automatic processor: FG660). The light source filter used was SC-41, available from Fuji Photo Film Co., Ltd.

These specimens were then evaluated for relative sensitivity, γ and letter image quality.

TABLE 4

| Coat Specimen No. | Emulsion | Dye | Added amount of dye (mg/m²) | Relative sensitivity | γ | Letter image quality |
|---|---|---|---|---|---|---|
| 5-1 | Z | Comparative Dye E | 20 | 100 | 13.0 | 3.5 |
| 5-2 | " | 15 | 70 | 99 | 13.5 | 5 |

The dye used for comparison was Comparative Dye E set forth as follows:

Comparative Dye E

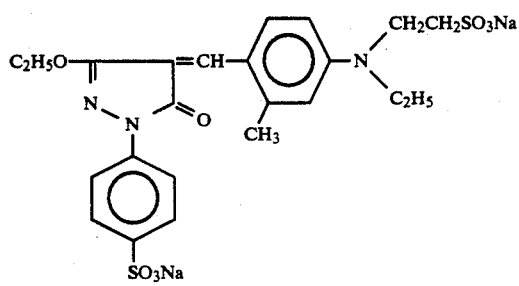

The comparison specimens were prepared according to Example 5 except Comparative Dye E was used instead of Compound 15.

Table 4 shows that the specimen of the present invention exhibits an excellent letter image quality.

EXAMPLE 6

Preparation of Specimen No. 6-1

A multilayer color light-sensitive material was prepared as Specimen 101 by coating various layers having the following compositions on an undercoated 127-μm thick cellulose triacetate film support. The figure indicates the added amount of each component per m². The effects of the compounds added are not limited to those described. 1st layer: antihalation layer

| 1st layer: antihalation layer | |
|---|---|
| Black colloidal silver | 0.25 g |
| Gelatin | 1.9 g |
| Ultraviolet absorbent U-1 | 0.04 g |
| Ultraviolet absorbent U-2 | 0.1 g |
| Ultraviolet absorbent U-3 | 0.1 g |
| Ultraviolet absorbent U-4 | 0.1 g |
| Ultraviolet absorbent U-6 | 0.1 g |
| High boiling organic solvent Oil-1 | 0.1 g |
| 2nd layer: interlayer | |
| Gelatin | 0.40 g |
| Compound Cpd-D | 10 mg |
| High boiling organic solvent Oil-3 | 0.1 g |
| Dye D-4 | 0.4 mg |
| 3rd layer: interlayer | |
| Emulsion of finely divided surface- and internally-fogged silver bromoiodide grains (average grain diameter: 0.06 μm; fluctuation coefficient: 18%; AgI content: 1 mol %) | 0.05 g (as calculated in terms of silver) |
| Gelatin | 0.4 g |
| 4th layer: low sensitivity red-sensitive emulsion layer | |
| Emulsion A | 0.2 g (as calculated in terms of silver) |
| Emulsion B | 0.3 g (as calculated in terms of silver) |
| Gelatin | 0.8 g |
| Coupler C-1 | 0.15 g |
| Coupler C-2 | 0.05 g |
| Coupler C-9 | 0.05 g |
| Compound Cpd-D | 10 mg |
| High boiling organic solvent Oil-2 | 0.1 g |
| 5th layer: middle sensitivity red-sensitive emulsion layer | |
| Emulsion B | 0.2 g (as calculated in terms of silver) |
| Emulsion C | 0.3 g (as calculated in terms of silver) |
| Gelatin | 0.8 g |
| Coupler C-1 | 0.2 g |
| Coupler C-2 | 0.05 g |
| Coupler C-3 | 0.2 g |
| High boiling organic solvent Oil-2 | 0.1 g |
| 6th layer: high sensitivity red-sensitive emulsion layer | |
| Emulsion D | 0.4 g (as calculated in terms of silver) |
| Gelatin | 1.1 g |
| Coupler C-1 | 0.3 g |
| Coupler C-3 | 0.7 g |
| Additive P-1 | 0.1 g |
| 7th layer: interlayer | |
| Gelatin | 0.6 g |
| Additive M-1 | 0.3 g |
| Color stain inhibitor Cpd-K | 2.6 mg |
| Ultraviolet absorbent U-1 | 0.1 g |
| Ultraviolet absorbent U-6 | 0.1 g |
| Dye D-1 | 0.02 g |
| 8th layer: interlayer | |
| Emulsion of surface- and internally-fogged silver bromoiodide grains (average grain diameter: 0.06 μm; fluctuation coefficient: 16%; AgI content: 0.3 mol %) | 0.02 g (as calculated in terms of silver) |
| Gelatin | 1.0 g |
| Additive P-1 | 0.2 g |
| Color stain inhibitor Cpd-J | 0.1 g |
| Color stain inhibitor Cpd-A | 0.1 g |
| 9th layer: low sensitivity green-sensitive emulsion layer | |
| Emulsion E | 0.3 g (as calculated in terms of silver) |
| Emulsion F | 0.1 g (as calculated in terms of silver) |
| Emulsion G | 0.1 g (as calculated in terms of silver) |
| Gelatin | 0.5 g |
| Coupler C-7 | 0.05 g |
| Coupler C-8 | 0.20 g |
| Compound Cpd-B | 0.03 g |
| Compound Cpd-D | 10 mg |
| Compound Cpd-E | 0.02 g |

| | | |
|---|---|---|
| Compound Cpd-F | 0.02 g | |
| Compound Cpd-G | 0.02 g | |
| Compound Cpd-H | 0.02 g | |
| High boiling organic solvent Oil-1 | 0.1 g | |
| High boiling organic solvent Oil-2 | 0.1 g | |
| 10th layer: middle sensitivity green-sensitive emulsion layer | | |
| Emulsion G | 0.3 g (as calculated in terms of silver) | |
| Emulsion H | 0.1 g (as calculated in terms of silver) | |
| Gelatin | 0.6 g | |
| Coupler C-7 | 0.2 g | |
| Coupler C-8 | 0.1 g | |
| Compound Cpd-B | 0.03 g | |
| Compound Cpd-E | 0.02 g | |
| Compound Cpd-F | 0.02 g | |
| Compound Cpd-G | 0.05 g | |
| Compound Cpd-H | 0.05 g | |
| High boiling organic solvent Oil-2 | 0.01 g | |
| 11th layer: high sensitivity green-sensitive emulsion layer | | |
| Emulsion I | 0.5 g (as calculated in terms of silver) | |
| Gelatin | 1.0 g | |
| Coupler C-4 | 0.3 g | |
| Coupler C-8 | 0.1 g | |
| Compound Cpd-B | 0.08 g | |
| Compound Cpd-E | 0.02 g | |
| Compound Cpd-F | 0.02 g | |
| Compound Cpd-G | 0.02 g | |
| Compound Cpd-H | 0.02 g | |
| High boiling organic solvent Oil-1 | 0.02 g | |
| High boiling organic solvent Oil-2 | 0.02 g | |
| 12th layer: interlayer | | |
| Gelatin | 0.6 g | |
| Dye D-1 | 0.1 g | |
| Dye D-2 | 0.05 g | |
| Dye D-3 | 0.07 g | |
| 13th layer: yellow filter layer | | |
| Yellow colloidal silver | 0.1 g (as calculated in terms of silver) | |
| Gelatin | 1.1 g | |
| Color stain inhibitor Cpd-A | 0.01 g | |
| High boiling organic solvent Oil-1 | 0.01 g | |
| 14th layer: interlayer | | |
| Gelatin | 0.6 g | |
| 15th layer: low sensitivity blue-sensitive emulsion layer | | |
| Emulsion J | 0.4 g (as calculated in terms of silver) | |
| Emulsion K | 0.1 g (as calculated in terms of silver) | |
| Emulsion L | 0.1 g (as calculated in terms of silver) | |
| Gelatin | 0.8 g | |
| Coupler C-5 | 0.6 g | |
| 16th layer: middle sensitivity blue-sensitive emulsion layer | | |
| Emulsion L | 0.1 g (as calculated in terms of silver) | |
| Emulsion M | 0.4 g (as calculated in terms of silver) | |
| Gelatin | 0.9 g | |
| Coupler C-5 | 0.3 g | |
| Coupler C-6 | 0.3 g | |
| 17th layer: high sensitivity blue-sensitive emulsion layer | | |
| Emulsion N | 0.4 g (as calculated in terms of silver) | |
| Gelatin | 1.2 g | |
| Coupler C-6 | 0.7 g | |
| 18th layer: 1st protective layer | | |
| Gelatin | 0.7 g | |
| Ultraviolet absorbent U-1 | 0.04 g | |
| Ultraviolet absorbent U-2 | 0.01 g | |
| Ultraviolet absorbent U-3 | 0.03 g | |
| Ultraviolet absorbent U-4 | 0.03 g | |
| Ultraviolet absorbent U-5 | 0.05 g | |
| Ultraviolet absorbent U-6 | 0.05 g | |
| High boiling organic solvent Oil-1 | 0.02 g | |
| Formalin scavenger Compound Cpd-C | 0.2 g | |
| Compound Cpd-I | 0.4 g | |
| Dye D-3 | 0.05 g | |
| 19th layer: 2nd protective layer | | |
| Colloidal silver | 0.1 mg (as calculated in terms of silver) | |
| Emulsion of finely divided silver bromoiodide grains (average grain diameter: 0.06 μm; AgI content: 1 mol %) | 0.1 g (as calculated in terms of silver) | |
| Gelatin | 0.4 g | |
| 20th layer: 3rd protective layer | | |
| Gelatin | 0.4 g | |
| Polymethyl methacrylate (average grain diameter: 1.5 μm) | 0.1 g | |
| 4:6 Copolymer of methyl methacrylate and acrylic acid (average grain diameter: 1.5 μm) | 0.1 g | |
| Silicone oil | 0.03 g | |
| Surface active agent W-1 | 3.0 mg | |
| Surface active agent W-2 | 0.03 g | |

Additives F-1 to F-8 we added to all the emulsion layers besides the above mentioned compositions. A gelatin hardener, H-1, surface active agents W-3 and W-4 for coating aid and emulsion aid were also added to each of these layers besides the above mentioned compositions.

Examples of preservatives and fungicides added to these layers include phenol, 1,2-benzisothiazoline-3-one, 2-phenoxyethanol and phenethyl alcohol.

Silver bromoiodide emulsions A-N incorporated in Specimen 6-1 were as follows:

| | Emulsion | Average grain diameter (μm) | Fluctuation coefficient (%) | AgI content (%) |
|---|---|---|---|---|
| A | Monodisperse emulsion of tetradecahedral grains | 0.25 | 16 | 3.7 |
| B | Monodisperse emulsion of internal latent image type cubic grains | 0.30 | 10 | 3.3 |
| C | Monodisperse emulsion of tetradecahedral grains | 0.30 | 18 | 5.0 |
| D | Polydisperse emulsion of twin grains | 0.60 | 25 | 2.0 |
| E | Monodisperse emulsion of cubic grains | 0.17 | 17 | 4.0 |
| F | Monodisperse emulsion of cubic grains | 0.20 | 16 | 4.0 |
| G | Monodisperse emulsion of | | | |

| Emulsion | Average grain diameter (μm) | Fluctuation coefficient (%) | AgI content (%) |
|---|---|---|---|
| internal latent image type cubic grains | 0.25 | 11 | 3.5 |
| H Monodisperse emulsion of internal latent image type cubic grains | 0.30 | 9 | 3.5 |
| I Polydisperse emulsion of tabular grains (average aspect ratio: 4.0) | 0.80 | 28 | 1.5 |
| J Monodisperse emulsion of tetradecahedral grains | 0.30 | 18 | 4.0 |
| K Monodisperse emulsion of tetradecahedral grains | 0.37 | 17 | 4.0 |
| L Monodisperse emulsion of internal latent image type cubic grains | 0.46 | 14 | 3.5 |
| M Monodisperse emulsion of cubic grains | 0.55 | 13 | 4.0 |
| N Polydisperse emulsion of tabular grains (average aspect ratio: 7.0) | 1.00 | 33 | 1.3 |

Spectral Sensitization of Emulsions A–N

| Emulsion | Added sensitizing dye | Added amount (g) per mol of silver halide | Time when sensitizing dye was added |
|---|---|---|---|
| A | S-1 | 0.025 | Shortly after chemical sensitization |
|   | S-2 | 0.25 | Shortly after chemical sensitization |
| B | S-1 | 0.01 | Shortly after grain formation |
|   | S-2 | 0.25 | Shortly after grain formation |
| C | S-1 | 0.02 | Shortly after chemical sensitization |
|   | S-2 | 0.25 | Shortly after chemical sensitization |
| D | S-1 | 0.01 | Shortly after chemical sensitization |
|   | S-2 | 0.10 | Shortly after chemical sensitization |
|   | S-7 | 0.01 | Shortly after chemical sensitization |
| E | S-3 | 0.5 | Shortly after chemical sensitization |
|   | S-4 | 0.1 | Shortly after chemical sensitization |
| F | S-3 | 0.3 | Shortly after chemical sensitization |
|   | S-4 | 0.1 | Shortly after chemical sensitization |
| G | S-3 | 0.25 | Shortly after grain formation |
|   | S-4 | 0.08 | Shortly after grain formation |
| H | S-3 | 0.2 | During grain formation |
|   | S-4 | 0.06 | During grain formation |
| I | S-3 | 0.3 | Shortly before chemical sensitization |
|   | S-4 | 0.07 | Shortly before chemical sensitization |
|   | S-8 | 0.1 | Shortly before chemical sensitization |
| J | S-6 | 0.2 | During grain formation |
|   | S-5 | 0.05 | During grain formation |
| K | S-6 | 0.2 | During grain formation |
|   | S-5 | 0.05 | During grain formation |
| L | S-6 | 0.22 | Shortly after grain formation |
|   | S-5 | 0.06 | Shortly after grain formation |
| M | S-6 | 0.15 | Shortly after chemical sensitization |
|   | S-5 | 0.04 | Shortly after chemical sensitization |
| N | S-6 | 0.22 | Shortly after grain formation |
|   | S-5 | 0.06 | Shortly after grain formation |

C-1
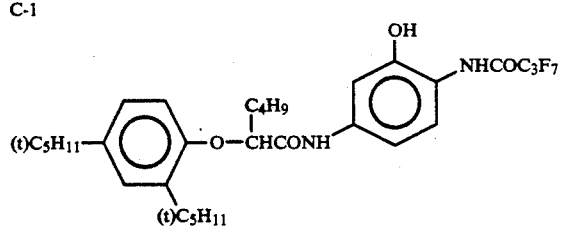

C-2
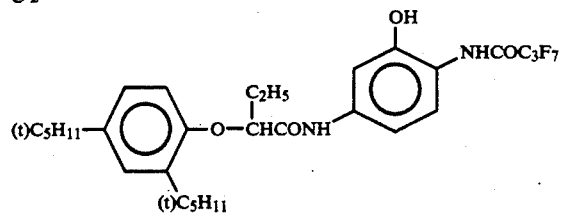

C-3
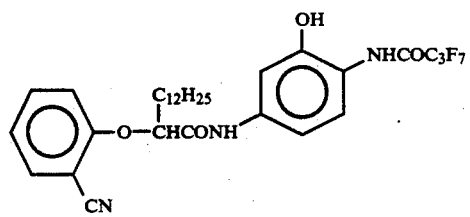

C-4
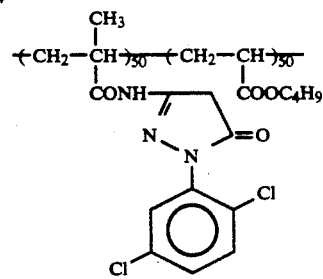

number: by weight
Average molecular weight: approx. 25,000

-continued
C-5
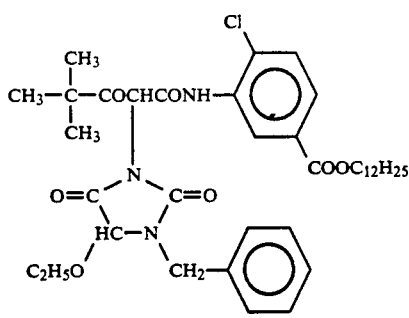
C-6
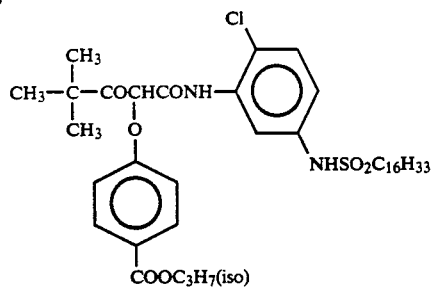
C-7
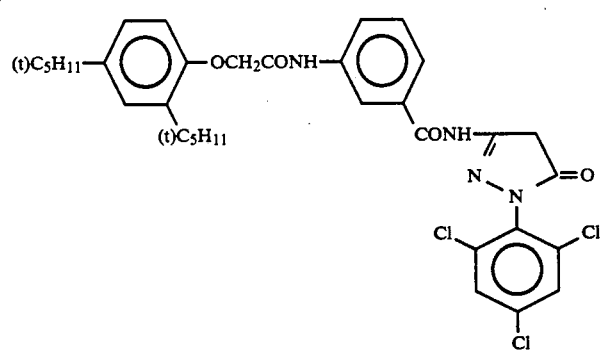
C-8
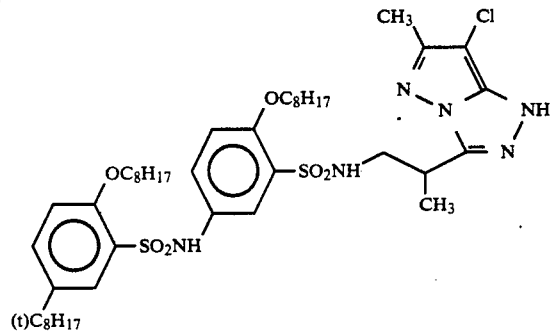
C-9
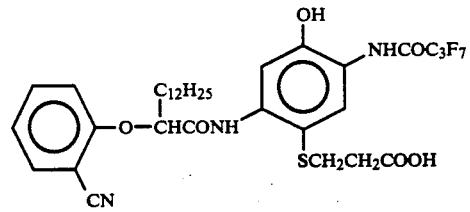
Oil-1 Dibutyl phthalate    Oil-2 Tricresyl phosphate    Oil-3 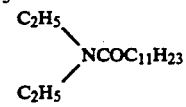
Cpd-A
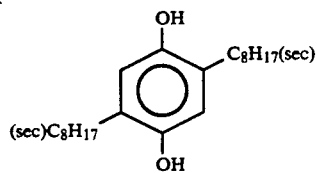
Cpd-B
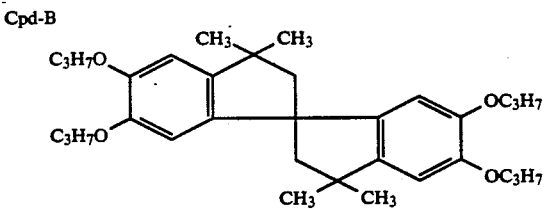

Cpd-C 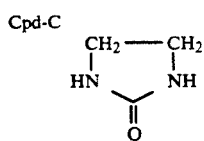
Cpd-D 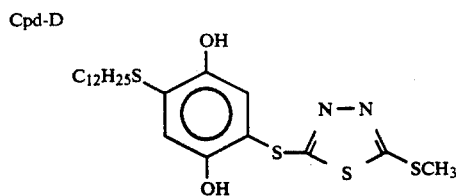
Cpd-E 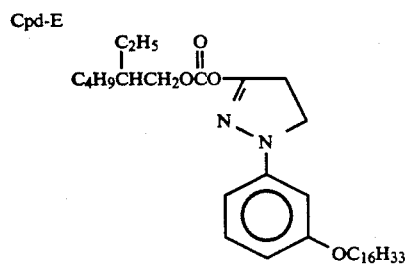
Cpd-F 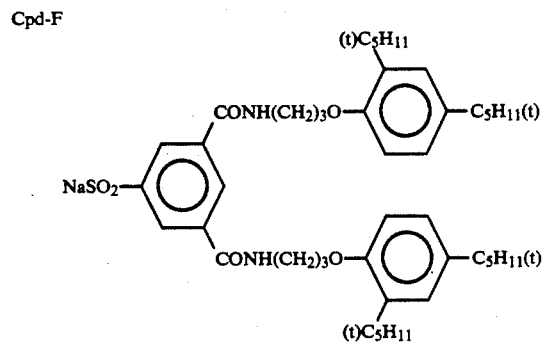
Cpd-G 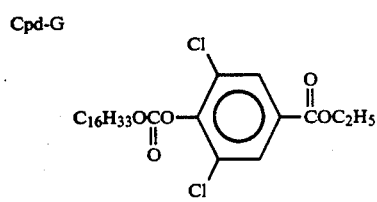
Cpd-H 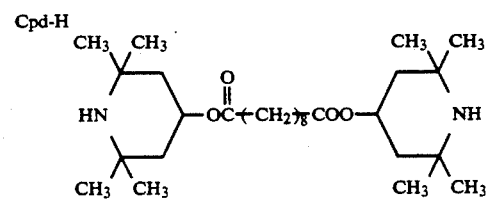
Cpd-I 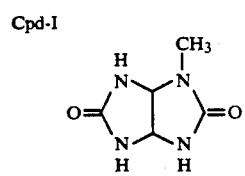
Cpd-J 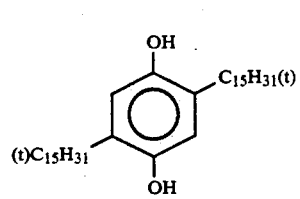
Cpd-K 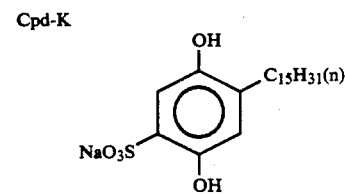
U-1 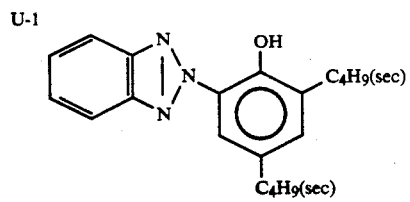
U-2 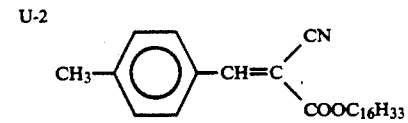
U-3 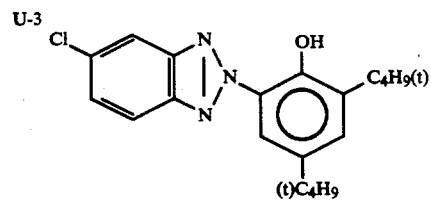
U-4 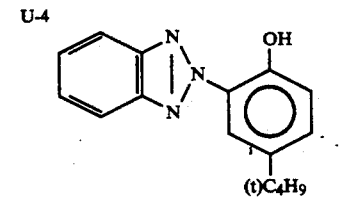
U-5 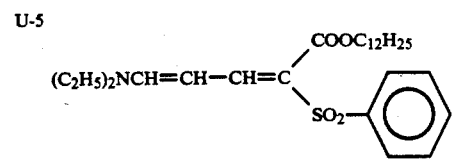
U-6 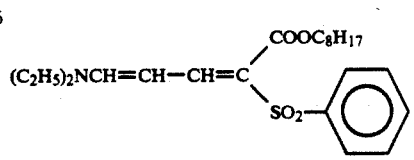

-continued
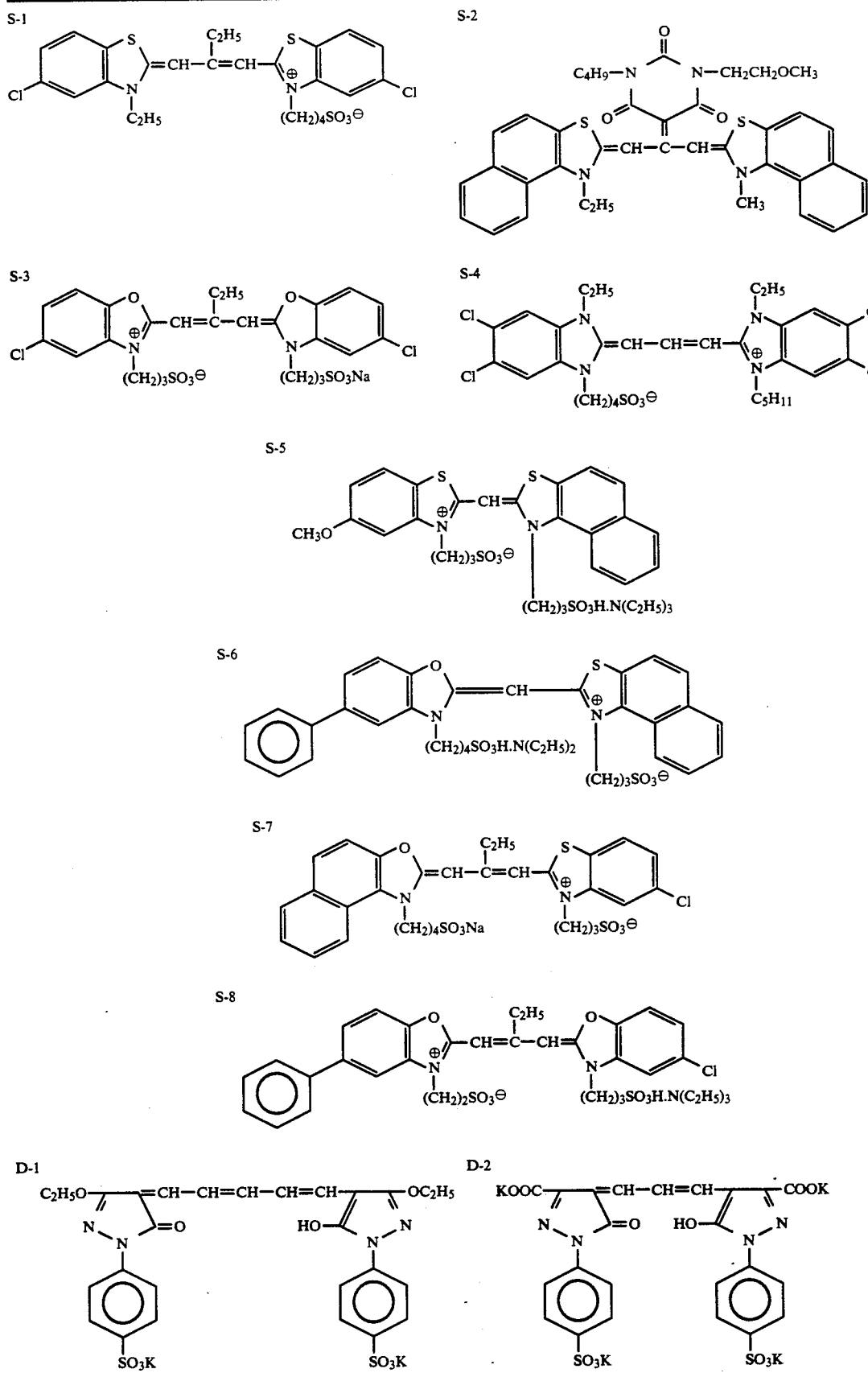

-continued

D-3: pyrazolone dye — 4-[(4-sulfonatophenyl)azo]-5-hydroxy-1-(4-sulfonatophenyl)-1H-pyrazole-3-carboxylate, disodium salt D-4: 2-[(2,4-di-tert-pentylphenoxy)propylcarbamoyl]-4-[(4-diethylamino-2-methylphenyl)imino]-1(4H)-naphthalenone H-1:
CH$_2$=CH—SO$_2$—CH$_2$—CONH—CH$_2$
CH$_2$=CH—SO$_2$—CH$_2$—CONH—CH$_2$
(the two CH$_2$ groups linked)

W-1: C$_8$F$_{17}$SO$_2$NHCH$_2$CH$_2$CH$_2$OCH$_2$CH$_2$N$^\oplus$(CH$_3$)$_3$ · CH$_3$-C$_6$H$_4$-SO$_3^\ominus$

W-2: C$_8$F$_{17}$SO$_2$N(C$_3$H$_7$)CH$_2$COOK

W-3:
NaO$_3$S—CH(COOCH$_2$CH(C$_2$H$_5$)C$_4$H$_9$)—CH$_2$COOCH$_2$CH(C$_2$H$_5$)C$_4$H$_9$

W-4: C$_8$H$_{17}$—C$_6$H$_4$—(OCH$_2$CH$_2$)$_3$SO$_3$Na

P-1: —(CH$_2$—CH)$_n$— with CONHC$_4$H$_9$(t) side group

P-2: —(CH$_2$—CH)$_n$— with COOC$_4$H$_9$ side group

F-1: 5-methyl-7-hydroxy-s-triazolo[1,5-a]pyrimidine

F-2: [triazine-based polymer with —CH(CH$_2$)$_3$—NH— linkage and —NHCH$_2$CH$_2$OH substituent]$_n$ · HNO$_3$ F-3: 2-mercapto-5-(methylthio)-1,3,4-thiadiazole (HS—C=N—N=C(SCH$_3$)—S—)

F-4: 1-phenyl-5-mercapto-tetrazole

F-5: 1-[3-(N'-methylureido)phenyl]-5-mercaptotetrazole

F-6: hydroquinone (1,4-dihydroxybenzene)

-continued

F-7 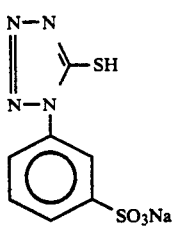

F-8 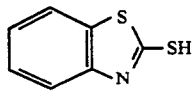

Comparative Specimen No. 6-2 was prepared in the same manner as in Specimen No. 6-1 except that the yellow colloidal silver incorporated in the 13th layer was replaced by the following dye as disclosed in International Patent Application Disclosure 88/04794 in the form of a disperse solid prepared with a surface active agent and water in a ball mill in accordance with the above cited patent application in an amount of 0.175 g/m².

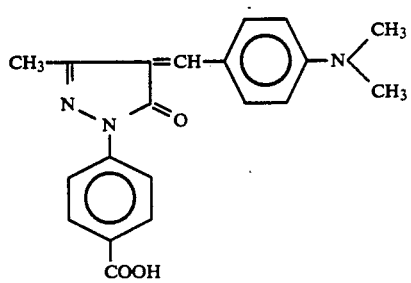

Further, Specimen No. 6-3 was prepared in the same manner as in Specimen No. 6-1 except that the yellow colloidal silver incorporated in the 13th layer was replaced by a dispersion of 0.230 g/m² of Compound (1) with 0.19 g/m² of the following surface active agent:

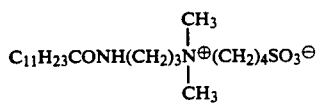

The dispersion was effected in the same manner as in Example 1.

Moreover, Specimen No. 6-4 was prepared in the same manner as in Specimen No. 6-1 except that the black colloidal silver incorporated in the 1st layer as an antihalation layer was replaced by the following dye as described in JP-A-52-92716:

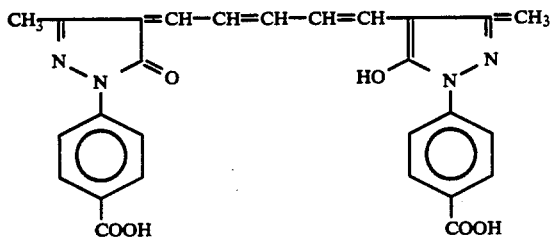

in the form of a disperse solid prepared with water and a surface active agent Triton X-200 in a ball mill and the yellow colloidal silver incorporated in the 13th layer was the same as used in Specimen No. 6-3.

These specimens were cut into strips. These strips were imagewise exposed to light, subjected to the following development at a temperature of 38° C., and then measured for density.

| Processing step | Processing Time | Temp. | Tank capacity | Replenishment rate |
|---|---|---|---|---|
| Black-and-white development | 6 min. | 38° C. | 12 l | 2.2 l/m² |
| 1st Rinse | 2 min. | 38° C. | 4 l | 7.5 l/m² |
| Reversal | 2 min. | 38° C. | 4 l | 1.1 l/m² |
| Color development | 6 min. | 38° C. | 12 l | 2.2 l/m² |
| Bleach | 3 min. | 38° C. | 6 l | 0.15 l/m² |
| Fixing | 4 min. | 38° C. | 8 l | 2.2 l/m² |
| 2nd Rinse (1) | 2 min. | 38° C. | 4 l | — |
| 2nd Rinse (2) | 2 min. | 38° C. | 4 l | 7.5 l/m² |
| Stabilizing | 2 min. | 38° C. | 4 l | 1.1 l/m² |
| 3rd Rinse | 1 min. | 38° C. | 4 l | 1.1 l/m² |

The overflow solution from the 2nd rinse (2) bath was introduced into the 2nd rinse (1) bath.

| | Running Solution | Replenisher |
|---|---|---|
| Black-and-white developer | | |
| Pentasodium nitrilo-N,N,N-trimethylenephosphonate | 2.0 g | 2.0 g |
| Pentasodium deithylenetriamine-pentaacetate | 3.0 g | 3.0 g |
| Potassium sulfite | 30.0 g | 30.0 g |
| Potassium hydroquinone monosulfonate | 20.0 g | 20.0 g |
| Potassium carbonate | 33.0 g | 33.0 g |
| 1-Phenyl-4-methyl-4-hydroxymethyl-3-pyrazolidone | 2.0 g | 2.0 g |
| Potassium bromide | 2.5 g | 1.4 g |
| Potassium thiocyanate | 1.2 g | 1.2 g |
| Potassium iodide | 2.0 mg | 2.0 mg |
| Water to make | 1.0 l | 1.0 l |
| pH (25° C.) adjusted with hydrochloric acid or potassium hydroxide | 9.60 | 9.70 |
| Reversing solution | | |
| Pentasodium nitrilo-N,N,N-trimethylenephosphonate | 3.0 g | Amount which is left |
| Stannous chloride dihydrate | 1.0 g | Amount which is left |
| p-Aminophenol | 0.1 g | Amount which is left |
| Sodium hydroxide | 8.0 g | Amount which is left |
| Glacial acetic acid | 15.0 ml | Amount which is left |
| Water to make | 1.0 l | Amount which is left |
| pH (25° C.) with hydrochloric acid or sodium hydroxide | 6.00 | Amount which is left |
| Color developer | | |
| Pentasodium nitrilo-N,N,N-trimethylenephosphonate | 2.0 g | 2.0 g |

-continued

| | | |
|---|---|---|
| Pentasodium diethylene-triaminepentaacetate | 2.0 g | 2.0 g |
| Sodium sulfate | 7.0 g | 7.0 g |
| Tripotassium phosphate dodecahydrate | 36.0 g | 36.0 g |
| Potassium bromide | 1.0 g | — |
| Potassium iodide | 90.0 mg | — |
| Sodium hydroxide | 3.0 g | 3.0 g |
| Citrazinic acid | 1.5 g | 1.5 g |
| N-ethyl-(β-methanesulfonamideethyl)-3-methyl-4-aminoaniline sulfate | 10.5 g | 10.5 g |
| 3,6-Dithiaoctane-1,8-diol | 3.5 g | 3.5 g |
| Water to make | 1.0 l | 1.0 l |
| pH (25° C.) adjusted with hydrochloric acid or potassium hydroxide | 11.90 | 12.05 |
| Bleaching solution | | |
| 1,3-Diaminopropanetetraacetic acid | 2.8 g | 4.0 g |
| Ferric ammonium 1,3-monohydrate | 138.0 g | 207.0 g |
| Ammonium bromide | 80.0 g | 120.0 g |
| Ammonium sulfate | 20.0 g | 30.0 g |
| Hydroxyacetic acid | 50.0 g | 75.0 g |
| Acetic acid | 50.0 g | 75.0 g |
| Water to make | 1.0 l | 1.0 l |
| pH (25° C.) adjusted with acetic acid or aqueous ammonia | 3.40 | 2.80 |
| Fixing solution | | |
| Disodium ethylenediamine-tetraacetate dihydrate | 1.7 g | Amount which is left |
| Sodium benzaldehyde-o-sulfonate | 20.0 g | Amount which is left |
| Sodium bisulfite | 15.0 g | Amount which is left |
| Ammonium thiosulfate (700 g/l) | 340.0 ml | Amount which is left |
| Imidazole | 28.0 g | Amount which is left |
| Water to make | 1.0 l | Amount which is left |
| pH (25° C.) adjusted with acetic acid or aqueous ammonia | 4.00 | Amount which is left |
| Stabilizing Solution | | |
| Disodium ethylenediamine-tetraacetate dihydrate | 1.0 g | Amount which is left |
| Sodium carbonate | 6.0 g | Amount which is left |
| 37% Formalin | 5.0 ml | Amount which is left |
| Water to make | 1.0 l | Amount which is left |
| pH (25° C.) adjusted with acetic acid or sodium hydroxide | 10.00 | Amount which is left |
| 3rd Rinse Solution | | |
| Disodium ethylenediamine-tetraacetate dihydrate | 0.2 g | Amount which is left |
| Hydroxyethylidene-1,1-diphosphonic acid | 0.05 g | Amount which is left |
| Ammonium acetate | 2.0 g | Amount which is left |
| Sodium dodecylbenzenesulfonate | 0.3 g | Amount which is left |
| pH (25° C.) adjusted with acetic acid or aqueous ammonia | 4.50 | Amount which is left |

TABLE 5

| Specimen No. | Relative Sensitivity | | | Maximum Density | | |
|---|---|---|---|---|---|---|
| | Blue | Green | Red | Blue | Green | Red |
| 6-1 (Comparison) | ±0 | ±0 | ±0 | ±0 | ±0 | ±0 |
| 6-2 (Comparison) | +0.01 | −0.03 | −0.04 | +0.28 | +0.25 | +0.04 |
| 6-3 (Invention) | +0.01 | +0.06 | +0.02 | +0.29 | +0.25 | +0.05 |
| 6-4 (Invention) | +0.00 | +0.06 | +0.02 | +0.27 | +0.26 | +0.14 |

Table 5 shows that since the compounds of the present invention have little effect on the silver halide emulsion and thus provide a high minimum density and a sharp absorption, the sensitivity of the layers under the filter layer comprising these compounds are higher than that of the filter layer of the comparative examples.

While the invention has been described in detail and with reference to specific embodiments thereof, it will be apparent to one skilled in the art that various changes and modifications can be made therein without departing from the spirit and scope thereof.

What is claimed is:

1. A silver halide photographic material comprising at least one silver halide emulsion layer on a support, wherein said emulsion layer or other hydrophilic colloid layers comprise at least one compound represented by formula:

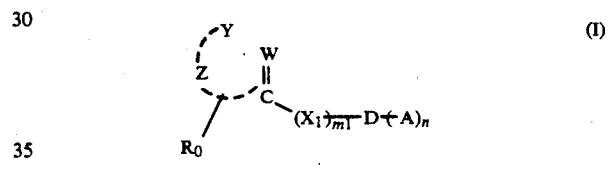

wherein W represents =N— or

in which $R_1$ represents a hydrogen atom or a substituent; $R_0$ represents an alkyl group containing 10 or more carbon atoms or an aromatic group containing 12 or more carbon atoms; Z represents an atomic group which can form a heterocyclic group or a carbon ring; Y represents

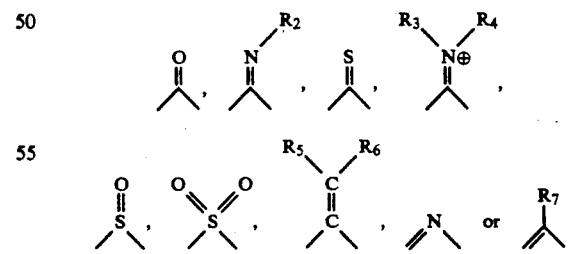

wherein $R_2$, $R_3$, $R_4$, $R_5$, $R_6$ and $R_7$ each represents a hydrogen atom or a substituent; $X_1$ represents a divalent group connected to carbon atom via a hetero atom contained therein; D represents a photographic dye portion connected to $X_1$ via a hetero atom contained therein; A represents a water-solubilizing group; $m_1$ represents an integer 0 or 1; and n represents an integer 2 or more.

2. A silver halide photographic material as in claim 1, wherein the compound represented by formula (I) is used in an amount giving rise to an optical density of 0.05 to 3.0.

3. A silver halide photographic material as in claim 1, wherein the compound represented by formula (I) is used in an amount of $10^{-3}$ g/m$^2$ to 3.0 g/m$^2$.

4. A silver halide photographic material as in claim 3, wherein the amount is $10^{-3}$ g/m$^2$ to 1.0 g/m$^2$.

5. A silver halide photographic material as in claim 1, wherein the compound represented by formula (I) is incorporated in at least one of a subbing layer, an antihalation layer provided between a silver halide emulsion layer and a support, a silver halide emulsion layer, an interlayer, a protective layer, a back layer on the side of the support opposite a silver halide emulsion layer, and other auxiliary layers.

* * * * *